(12) United States Patent
Hartwell

(10) Patent No.: US 12,290,627 B2
(45) Date of Patent: May 6, 2025

(54) WOUND DRESSING

(71) Applicant: Smith & Nephew PLC, Watford (GB)

(72) Inventor: Edward Yerbury Hartwell, Hull (GB)

(73) Assignee: Smith & Nephew PLC, Watford (GB)

( * ) Notice: Subject to any disclaimer, the term of this patent is extended or adjusted under 35 U.S.C. 154(b) by 809 days.

(21) Appl. No.: 17/466,406

(22) Filed: Sep. 3, 2021

(65) Prior Publication Data

US 2022/0000673 A1   Jan. 6, 2022

Related U.S. Application Data

(63) Continuation of application No. 16/186,393, filed on Nov. 9, 2018, now Pat. No. 11,110,010, which is a
(Continued)

(30) Foreign Application Priority Data

Nov. 21, 2007  (GB) ...................................... 0722820
Sep. 17, 2008  (GB) ...................................... 0817040

(51) Int. Cl.
*A61M 1/00*     (2006.01)
*A61F 13/00*    (2024.01)
(Continued)

(52) U.S. Cl.
CPC ....... *A61M 1/962* (2021.05); *A61F 13/00063* (2013.01); *A61F 13/02* (2013.01); *A61F 13/0206* (2013.01); *A61F 13/0209* (2013.01); *A61F 13/022* (2013.01); *A61F 13/0226* (2013.01); *A61F 13/0246* (2013.01);
(Continued)

(58) Field of Classification Search
CPC .......... A61F 13/00063; A61F 13/01029; A61F 13/01046; A61F 13/02; A61F 13/0206; A61F 13/0209; A61F 13/022; A61F 13/0226; A61F 13/0246; A61F 13/05; A61F 2013/00246; A61F 2013/00536; A61M 1/71; A61M 1/78; A61M 1/784; A61M 1/882; A61M 1/915; A61M 1/962;
(Continued)

(56) References Cited

U.S. PATENT DOCUMENTS

| | | |
|---|---|---|
| 695,270 A | 3/1902 | Beringer |
| 1,480,562 A | 1/1924 | Hugo et al. |

(Continued)

FOREIGN PATENT DOCUMENTS

| | | |
|---|---|---|
| CN | 2186074 Y | 12/1994 |
| DE | 847475 C | 8/1952 |

(Continued)

OTHER PUBLICATIONS

US 6,216,701 B1, 04/2001, Heaton et al. (withdrawn)
(Continued)

*Primary Examiner* — Andrew J Mensh
(74) *Attorney, Agent, or Firm* — Knobbe, Martens, Olson & Bear, LLP

(57) ABSTRACT

A method and apparatus are disclosed for dressing a wound. The apparatus comprises a sealing layer comprising at least one orifice, an absorbent layer over the sealing layer, absorbing wound exude and a liquid impermeable, gas permeable filter layer over the absorbent layer.

9 Claims, 3 Drawing Sheets

Related U.S. Application Data continuation of application No. 14/692,622, filed on Apr. 21, 2015, now Pat. No. 10,123,909, which is a continuation of application No. 14/276,983, filed on May 13, 2014, now Pat. No. 9,220,822, which is a continuation of application No. 12/744,218, filed as application No. PCT/GB2008/051089 on Nov. 20, 2008, now Pat. No. 8,808,274.

(51) Int. Cl.
| | |
|---|---|
| *A61F 13/02* | (2006.01) |
| *A61F 13/0203* | (2024.01) |
| *A61F 13/0206* | (2024.01) |
| *A61F 13/0246* | (2024.01) |
| *A61F 13/05* | (2024.01) |
| *A61M 27/00* | (2006.01) |
| *A61F 13/01* | (2024.01) |

(52) U.S. Cl.
CPC ............... *A61F 13/05* (2024.01); *A61M 1/71* (2021.05); *A61M 1/78* (2021.05); *A61M 1/784* (2021.05); *A61M 1/964* (2021.05); *A61M 1/985* (2021.05); *A61M 27/00* (2013.01); *A61F 2013/00246* (2013.01); *A61F 2013/00536* (2013.01); *A61F 13/01029* (2024.01); *A61F 13/01046* (2024.01); *A61M 1/882* (2021.05); *A61M 2205/7527* (2013.01); *A61M 2205/7536* (2013.01)

(58) Field of Classification Search
CPC ...... A61M 1/964; A61M 1/985; A61M 27/00; A61M 2205/7527; A61M 2205/7536
See application file for complete search history.

(56) References Cited

U.S. PATENT DOCUMENTS

| | | | |
|---|---|---|---|
| 1,969,880 | A | 8/1934 | Powell et al. |
| 2,280,915 | A | 4/1942 | Johnson |
| 2,367,690 | A | 1/1945 | Purdy |
| 2,568,933 | A | 9/1951 | Robbins |
| 2,632,443 | A | 3/1953 | Lesher |
| 2,682,873 | A | 7/1954 | Idnis et al. |
| 2,910,763 | A | 11/1959 | Lauterbach |
| 3,115,138 | A | 12/1963 | McElvenny et al. |
| 3,367,332 | A | 2/1968 | Groves |
| 3,572,340 | A | 3/1971 | Lloyd et al. |
| 3,874,387 | A | 4/1975 | Barbieri |
| 3,972,328 | A | 8/1976 | Chen |
| 3,993,080 | A | 11/1976 | Loseff |
| 4,029,598 | A | 6/1977 | Neisius et al. |
| RE29,319 | E | 7/1977 | Nordby et al. |
| 4,102,342 | A | 7/1978 | Akiyama et al. |
| 4,112,947 | A | 9/1978 | Nehring |
| 4,136,696 | A | 1/1979 | Nehring |
| 4,184,510 | A | 1/1980 | Murry et al. |
| 4,217,894 | A | 8/1980 | Franetzki |
| 4,219,019 | A | 8/1980 | Coates |
| 4,224,941 | A | 9/1980 | Stivala |
| 4,224,945 | A | 9/1980 | Cohen |
| 4,316,466 | A | 2/1982 | Babb |
| 4,382,441 | A | 5/1983 | Svedman |
| 4,398,910 | A | 8/1983 | Blake et al. |
| 4,465,485 | A | 8/1984 | Kashmer et al. |
| 4,534,356 | A | 8/1985 | Papadakis |
| 4,569,674 | A | 2/1986 | Phillips et al. |
| 4,573,965 | A | 3/1986 | Russo |
| 4,608,041 | A | 8/1986 | Nielsen |
| 4,624,656 | A | 11/1986 | Clark et al. |
| 4,655,754 | A | 4/1987 | Richmond et al. |
| 4,655,766 | A | 4/1987 | Theeuwes et al. |
| 4,681,562 | A | 7/1987 | Beck et al. |
| 4,710,165 | A | 12/1987 | McNeil et al. |
| 4,767,943 | A | 8/1988 | Adler et al. |
| 4,778,446 | A | 10/1988 | Jensen |
| 4,792,328 | A | 12/1988 | Beck et al. |
| 4,813,942 | A | 3/1989 | Alvarez |
| 4,826,494 | A | 5/1989 | Richmond et al. |
| 4,828,546 | A | 5/1989 | McNeil et al. |
| 4,921,488 | A | 5/1990 | Maitz et al. |
| 4,936,834 | A | 6/1990 | Beck et al. |
| 4,969,880 | A | 11/1990 | Zamierowski |
| 4,972,829 | A | 11/1990 | Knerr |
| 4,979,944 | A | 12/1990 | Luzsicza |
| 4,994,022 | A | 2/1991 | Steffler et al. |
| 5,055,195 | A | 10/1991 | Trasch et al. |
| 5,055,198 | A | 10/1991 | Shettigar |
| 5,056,510 | A | 10/1991 | Gilman |
| 5,060,642 | A | 10/1991 | Gilman |
| 5,073,172 | A | 12/1991 | Fell |
| 5,100,396 | A | 3/1992 | Zamierowski |
| 5,134,994 | A | 8/1992 | Say |
| 5,152,757 | A | 10/1992 | Eriksson |
| 5,167,613 | A | 12/1992 | Karami et al. |
| 5,176,663 | A | 1/1993 | Svedman et al. |
| 5,181,905 | A | 1/1993 | Flam |
| 5,215,519 | A | 6/1993 | Shettigar |
| 5,234,419 | A | 8/1993 | Bryant et al. |
| 5,238,732 | A | 8/1993 | Krishnan |
| 5,261,893 | A | 11/1993 | Zamierowski |
| 5,266,928 | A | 11/1993 | Johnson |
| 5,279,608 | A | 1/1994 | Cherif Cheikh |
| 5,328,614 | A | 7/1994 | Matsumura |
| 5,358,494 | A | 10/1994 | Svedman |
| 5,380,280 | A | 1/1995 | Peterson |
| D357,743 | S | 4/1995 | Bilitz et al. |
| 5,437,651 | A | 8/1995 | Todd et al. |
| 5,445,604 | A | 8/1995 | Lang |
| 5,489,280 | A | 2/1996 | Russell |
| 5,498,338 | A | 3/1996 | Kruger et al. |
| 5,527,293 | A | 6/1996 | Zamierowski |
| 5,536,233 | A | 7/1996 | Khouri |
| 5,549,584 | A | 8/1996 | Gross |
| 5,624,423 | A | 4/1997 | Anjur et al. |
| 5,632,731 | A | 5/1997 | Patel |
| 5,636,643 | A | 6/1997 | Argenta et al. |
| 5,643,189 | A | 7/1997 | Masini |
| 5,645,081 | A | 7/1997 | Argenta et al. |
| 5,662,583 | A | 9/1997 | Khouri |
| 5,676,634 | A | 10/1997 | Khouri |
| 5,678,564 | A | 10/1997 | Lawrence et al. |
| 5,695,445 | A | 12/1997 | Khouri |
| 5,700,477 | A | 12/1997 | Rosenthal et al. |
| 5,701,917 | A | 12/1997 | Khouri |
| 5,707,499 | A | 1/1998 | Joshi et al. |
| 5,733,337 | A | 3/1998 | Carr, Jr. et al. |
| 5,759,570 | A | 6/1998 | Arnold |
| 5,776,098 | A | 7/1998 | Silver et al. |
| 5,779,657 | A | 7/1998 | Daneshvar |
| 5,785,688 | A | 7/1998 | Joshi et al. |
| 5,817,145 | A | 10/1998 | Augustine et al. |
| 5,830,496 | A | 11/1998 | Freeman |
| 5,833,646 | A | 11/1998 | Masini |
| 5,843,011 | A | 12/1998 | Lucas |
| 5,868,933 | A | 2/1999 | Patrick et al. |
| 5,876,611 | A | 3/1999 | Shettigar |
| 5,902,256 | A | 5/1999 | Benaron |
| 5,964,723 | A | 10/1999 | Augustine |
| 6,010,527 | A | 1/2000 | Augustine et al. |
| 6,013,097 | A | 1/2000 | Augustine et al. |
| 6,071,267 | A | 6/2000 | Zamierowski |
| 6,093,160 | A | 7/2000 | Augustine et al. |
| 6,103,951 | A | 8/2000 | Freeman |
| 6,110,197 | A | 8/2000 | Augustine et al. |
| 6,117,111 | A | 9/2000 | Fleischmann |
| 6,135,116 | A | 10/2000 | Vogel et al. |
| 6,142,982 | A | 11/2000 | Hunt et al. |
| 6,168,800 | B1 | 1/2001 | Dobos et al. |
| 6,176,307 | B1 | 1/2001 | Danos et al. |
| 6,183,438 | B1 | 2/2001 | Berguer |
| 6,225,523 | B1 | 5/2001 | Masini |
| 6,248,084 | B1 | 6/2001 | Augustine et al. |

(56) References Cited

U.S. PATENT DOCUMENTS

| | | |
|---|---|---|
| 6,254,567 B1 | 7/2001 | Treu et al. |
| 6,255,552 B1 | 7/2001 | Cummings et al. |
| 6,257,847 B1 | 7/2001 | Silver et al. |
| 6,261,276 B1 | 7/2001 | Reitsma |
| 6,261,283 B1 | 7/2001 | Morgan et al. |
| 6,267,740 B1 | 7/2001 | Augustine et al. |
| 6,287,521 B1 | 9/2001 | Quay et al. |
| 6,291,050 B1 | 9/2001 | Cree et al. |
| 6,293,917 B1 | 9/2001 | Augustine et al. |
| 6,345,623 B1 | 2/2002 | Heaton et al. |
| 6,383,163 B1 | 5/2002 | Kelly et al. |
| 6,398,767 B1 | 6/2002 | Fleischmann |
| 6,402,724 B1 | 6/2002 | Smith et al. |
| 6,440,167 B2 | 8/2002 | Shimizu |
| 6,450,773 B1 | 9/2002 | Upton |
| 6,458,109 B1 | 10/2002 | Henley et al. |
| 6,465,708 B1 | 10/2002 | Augustine |
| 6,468,295 B2 | 10/2002 | Augustine et al. |
| 6,471,685 B1 | 10/2002 | Johnson |
| 6,471,982 B1 | 10/2002 | Lydon et al. |
| 6,481,986 B1 | 11/2002 | Silver et al. |
| 6,491,684 B1 | 12/2002 | Joshi et al. |
| 6,500,112 B1 | 12/2002 | Khouri |
| 6,547,756 B1 | 4/2003 | Greter et al. |
| 6,553,998 B2 | 4/2003 | Heaton et al. |
| 6,580,012 B1 | 6/2003 | Augustine et al. |
| 6,599,262 B1 | 7/2003 | Masini |
| 6,607,495 B1 | 8/2003 | Skalak et al. |
| 6,626,891 B2 | 9/2003 | Ohmstede |
| 6,638,270 B2 | 10/2003 | Johnson |
| 6,648,862 B2 | 11/2003 | Watson |
| 6,673,028 B1 | 1/2004 | Argenta et al. |
| 6,676,610 B2 | 1/2004 | Morton et al. |
| 6,676,631 B1 | 1/2004 | Greter |
| 6,685,681 B2 | 2/2004 | Lockwood et al. |
| 6,695,823 B1 | 2/2004 | Lina et al. |
| 6,695,824 B2 | 2/2004 | Howard et al. |
| 6,699,213 B1 | 3/2004 | Annis et al. |
| 6,752,794 B2 | 6/2004 | Lockwood et al. |
| 6,755,807 B2 | 6/2004 | Risk, Jr. et al. |
| 6,764,462 B2 | 7/2004 | Risk, Jr. et al. |
| 6,767,334 B1 | 7/2004 | Randolph |
| 6,775,807 B2 | 8/2004 | Lowther et al. |
| 6,787,682 B2 | 9/2004 | Gilman |
| 6,794,554 B2 | 9/2004 | Sessions et al. |
| 6,800,074 B2 | 10/2004 | Henley et al. |
| 6,808,517 B2 | 10/2004 | Greter et al. |
| 6,814,079 B2 | 11/2004 | Heaton et al. |
| 6,824,533 B2 | 11/2004 | Risk, Jr. et al. |
| 6,855,135 B2 | 2/2005 | Lockwood et al. |
| 6,856,821 B2 | 2/2005 | Johnson |
| 6,936,037 B2 | 8/2005 | Bubb et al. |
| 6,942,633 B2 | 9/2005 | Odland |
| 6,951,553 B2 | 10/2005 | Bubb et al. |
| 6,960,179 B2 | 11/2005 | Gura |
| 6,977,323 B1 | 12/2005 | Swenson |
| 6,979,324 B2 | 12/2005 | Bybordi et al. |
| 6,987,209 B2 | 1/2006 | Augustine et al. |
| 6,994,702 B1 | 2/2006 | Johnson |
| 6,997,897 B1 | 2/2006 | Silver et al. |
| 7,004,915 B2 | 2/2006 | Boynton et al. |
| 7,008,400 B2 | 3/2006 | Silver et al. |
| 7,022,113 B2 | 4/2006 | Lockwood et al. |
| 7,067,709 B2 | 6/2006 | Murata et al. |
| 7,070,584 B2 | 7/2006 | Johnson et al. |
| 7,077,832 B2 | 7/2006 | Fleischmann |
| 7,087,806 B2 | 8/2006 | Scheinberg et al. |
| 7,108,683 B2 | 9/2006 | Zamierowski |
| 7,117,869 B2 | 10/2006 | Heaton et al. |
| 7,122,046 B2 | 10/2006 | Augustine et al. |
| 7,128,735 B2 | 10/2006 | Weston |
| 7,141,714 B2 | 11/2006 | Nielsen |
| 7,182,085 B1 | 2/2007 | Larsen et al. |
| 7,195,624 B2 | 3/2007 | Lockwood et al. |
| 7,214,202 B1 | 5/2007 | Vogel et al. |
| 7,216,651 B2 | 5/2007 | Argenta et al. |
| 7,238,850 B2 | 7/2007 | Shimanuki |
| 7,255,681 B1 | 8/2007 | Silver et al. |
| 7,273,054 B2 | 9/2007 | Heaton et al. |
| 7,279,612 B1 | 10/2007 | Heaton et al. |
| 7,316,672 B1 | 1/2008 | Hunt et al. |
| 7,335,809 B2 | 2/2008 | Riesinger |
| 7,338,482 B2 | 3/2008 | Lockwood et al. |
| 7,361,184 B2 | 4/2008 | Joshi |
| 7,381,211 B2 | 6/2008 | Zamierowski |
| 7,381,859 B2 | 6/2008 | Hunt et al. |
| 7,438,705 B2 | 10/2008 | Karpowicz et al. |
| 7,470,830 B2 | 12/2008 | Sigurjonsson et al. |
| 7,485,112 B2 | 2/2009 | Karpowicz et al. |
| 7,494,482 B2 | 2/2009 | Orgill et al. |
| 7,503,910 B2 | 3/2009 | Adahan |
| 7,507,870 B2 | 3/2009 | Nielsen et al. |
| 7,524,286 B2 | 4/2009 | Johnson |
| 7,524,315 B2 | 4/2009 | Blott et al. |
| 7,534,240 B1 | 5/2009 | Johnson |
| 7,534,927 B2 | 5/2009 | Lockwood et al. |
| 7,553,306 B1 | 6/2009 | Hunt et al. |
| 7,569,742 B2 | 8/2009 | Haggstrom et al. |
| 7,601,129 B2 | 10/2009 | Aali |
| 7,605,298 B2 | 10/2009 | Bechert et al. |
| 7,611,500 B1 | 11/2009 | Lina et al. |
| 7,612,247 B2 | 11/2009 | Oyaski |
| 7,615,036 B2 | 11/2009 | Joshi et al. |
| 7,622,629 B2 | 11/2009 | Aali |
| D605,775 S | 12/2009 | Koch et al. |
| 7,625,362 B2 | 12/2009 | Boehringer et al. |
| D608,007 S | 1/2010 | Arbesman et al. |
| 7,645,253 B2 | 1/2010 | Gura et al. |
| 7,645,269 B2 | 1/2010 | Zamierowski |
| 7,670,323 B2 | 3/2010 | Hunt et al. |
| 7,678,090 B2 | 3/2010 | Risk, Jr. et al. |
| 7,687,678 B2 | 3/2010 | Jacobs |
| 7,699,823 B2 | 4/2010 | Haggstrom et al. |
| 7,699,830 B2 | 4/2010 | Martin |
| 7,700,819 B2 | 4/2010 | Ambrosio et al. |
| 7,708,724 B2 | 5/2010 | Weston |
| 7,717,313 B2 | 5/2010 | Criscuolo et al. |
| 7,718,249 B2 | 5/2010 | Russell et al. |
| 7,722,582 B2 | 5/2010 | Lina et al. |
| 7,731,702 B2 | 6/2010 | Bybordi et al. |
| 7,745,681 B1 | 6/2010 | Ferguson |
| 7,749,531 B2 | 7/2010 | Booher |
| 7,753,894 B2 | 7/2010 | Blott et al. |
| 7,754,936 B2 | 7/2010 | Heaton et al. |
| 7,758,514 B2 | 7/2010 | Grigoryants et al. |
| 7,758,554 B2 | 7/2010 | Lina et al. |
| 7,759,537 B2 | 7/2010 | Bishop et al. |
| 7,759,538 B2 | 7/2010 | Fleischmann |
| 7,759,539 B2 | 7/2010 | Shaw et al. |
| 7,763,000 B2 | 7/2010 | Risk, Jr. et al. |
| 7,775,998 B2 | 8/2010 | Riesinger |
| 7,776,028 B2 | 8/2010 | Miller et al. |
| 7,779,625 B2 | 8/2010 | Joshi et al. |
| 7,790,945 B1 | 9/2010 | Watson, Jr. |
| 7,790,946 B2 | 9/2010 | Mulligan |
| 7,794,438 B2 | 9/2010 | Henley et al. |
| 7,794,450 B2 | 9/2010 | Blott et al. |
| 7,803,980 B2 | 9/2010 | Griffiths et al. |
| 7,811,269 B2 | 10/2010 | Boynton et al. |
| 7,815,616 B2 | 10/2010 | Boehringer et al. |
| 7,816,577 B2 | 10/2010 | Aali |
| 7,828,782 B2 | 11/2010 | Suzuki |
| 7,830,980 B2 | 11/2010 | Li et al. |
| 7,838,716 B2 | 11/2010 | De Luis et al. |
| 7,838,717 B2 | 11/2010 | Haggstrom et al. |
| 7,846,141 B2 | 12/2010 | Weston |
| 7,857,806 B2 | 12/2010 | Karpowicz et al. |
| 7,858,838 B2 | 12/2010 | Holm et al. |
| 7,862,339 B2 | 1/2011 | Mulligan |
| 7,867,206 B2 | 1/2011 | Lockwood et al. |
| 7,880,050 B2 | 2/2011 | Robinson et al. |
| 7,884,258 B2 | 2/2011 | Boehringer et al. |
| 7,886,746 B2 | 2/2011 | Heaton et al. |
| 7,896,823 B2 | 3/2011 | Mangrum et al. |

(56) References Cited

U.S. PATENT DOCUMENTS

| | | |
|---|---|---|
| 7,896,856 B2 | 3/2011 | Petrosenko et al. |
| 7,909,805 B2 | 3/2011 | Weston |
| 7,910,791 B2 | 3/2011 | Coffey |
| 7,922,676 B2 | 4/2011 | Daskal et al. |
| 7,922,703 B2 | 4/2011 | Riesinger |
| 7,927,318 B2 | 4/2011 | Risk, Jr. et al. |
| 7,931,630 B2 | 4/2011 | Nishtala et al. |
| 7,942,866 B2 | 5/2011 | Radl et al. |
| 7,951,100 B2 | 5/2011 | Hunt et al. |
| 7,951,124 B2 | 5/2011 | Boehringer et al. |
| 7,959,624 B2 | 6/2011 | Riesinger |
| 7,964,766 B2 | 6/2011 | Blott et al. |
| 7,976,519 B2 | 7/2011 | Bubb et al. |
| D642,594 S | 8/2011 | Mattson et al. |
| 7,988,680 B2 | 8/2011 | Lockwood et al. |
| 7,998,125 B2 | 8/2011 | Weston |
| 8,007,257 B2 | 8/2011 | Heaton et al. |
| 8,007,481 B2 | 8/2011 | Schuessler et al. |
| 8,021,348 B2 | 9/2011 | Risk, Jr. et al. |
| 8,022,266 B2 | 9/2011 | Boehringer et al. |
| 8,025,650 B2 | 9/2011 | Anderson et al. |
| 8,034,037 B2 | 10/2011 | Adams et al. |
| 8,062,272 B2 | 11/2011 | Weston |
| 8,062,273 B2 | 11/2011 | Weston |
| 8,062,331 B2 | 11/2011 | Zamierowski |
| 8,080,702 B2 | 12/2011 | Blott et al. |
| 8,084,663 B2 | 12/2011 | Watson, Jr. |
| 8,092,441 B2 | 1/2012 | Sugito |
| 8,100,887 B2 | 1/2012 | Weston et al. |
| 8,105,295 B2 | 1/2012 | Blott et al. |
| 8,118,794 B2 | 2/2012 | Weston |
| 8,133,211 B2 | 3/2012 | Cavanaugh, II et al. |
| 8,152,785 B2 | 4/2012 | Vitaris |
| 8,158,844 B2 | 4/2012 | McNeil |
| 8,162,907 B2 | 4/2012 | Heagle |
| 8,162,909 B2 | 4/2012 | Blott et al. |
| 8,168,848 B2 | 5/2012 | Lockwood et al. |
| 8,207,392 B2 | 6/2012 | Haggstrom et al. |
| 8,211,071 B2 | 7/2012 | Mormino et al. |
| 8,212,100 B2 | 7/2012 | Moore |
| 8,215,929 B2 | 7/2012 | Shen et al. |
| 8,235,955 B2 | 8/2012 | Blott et al. |
| 8,241,261 B2 | 8/2012 | Randolph et al. |
| 8,251,979 B2 | 8/2012 | Malhi |
| 8,257,327 B2 | 9/2012 | Blott et al. |
| 8,257,328 B2 | 9/2012 | Augustine et al. |
| 8,282,611 B2 | 10/2012 | Weston |
| 8,303,552 B2 | 11/2012 | Weston |
| 8,308,714 B2 | 11/2012 | Weston et al. |
| 8,323,264 B2 | 12/2012 | Weston et al. |
| 8,348,910 B2 | 1/2013 | Blott et al. |
| 8,372,049 B2 | 2/2013 | Jaeb et al. |
| 8,382,731 B2 | 2/2013 | Johannison |
| 8,404,921 B2 | 3/2013 | Lee et al. |
| D679,819 S | 4/2013 | Peron |
| D679,820 S | 4/2013 | Peron |
| 8,419,696 B2 | 4/2013 | Wilkes |
| 8,425,478 B2 | 4/2013 | Olson |
| 8,439,894 B1 | 5/2013 | Miller |
| 8,444,612 B2 | 5/2013 | Patel et al. |
| 8,449,508 B2 | 5/2013 | Coulthard et al. |
| 8,494,349 B2 | 7/2013 | Gordon |
| 8,529,548 B2 | 9/2013 | Blott et al. |
| 8,545,464 B2 | 10/2013 | Weston |
| 8,545,466 B2 | 10/2013 | Andresen et al. |
| 8,568,386 B2 | 10/2013 | Malhi |
| 8,569,566 B2 | 10/2013 | Blott et al. |
| 8,603,074 B2 | 12/2013 | Kagan |
| 8,628,505 B2 | 1/2014 | Weston |
| 8,641,691 B2 | 2/2014 | Fink et al. |
| 8,702,665 B2 | 4/2014 | Locke et al. |
| 8,708,998 B2 | 4/2014 | Weston et al. |
| 8,715,256 B2 | 5/2014 | Greener |
| 8,795,243 B2 | 8/2014 | Weston |
| 8,795,244 B2 | 8/2014 | Randolph et al. |
| 8,808,274 B2 | 8/2014 | Hartwell |
| 8,814,842 B2 | 8/2014 | Coulthard et al. |
| 8,829,263 B2 | 9/2014 | Haggstrom et al. |
| 8,834,451 B2 | 9/2014 | Blott et al. |
| 8,834,452 B2 | 9/2014 | Hudspeth et al. |
| 8,905,985 B2 | 12/2014 | Allen et al. |
| 8,915,895 B2 | 12/2014 | Jaeb et al. |
| 8,956,336 B2 | 2/2015 | Haggstrom et al. |
| 8,974,429 B2 | 3/2015 | Gordon et al. |
| 9,050,209 B2 | 6/2015 | Coulthard et al. |
| 9,127,665 B2 | 9/2015 | Locke et al. |
| 9,220,822 B2 | 12/2015 | Hartwell |
| 9,265,867 B2 | 2/2016 | Coulthard et al. |
| 9,283,118 B2 | 3/2016 | Locke et al. |
| 9,302,033 B2 | 4/2016 | Riesinger |
| 9,375,353 B2 | 6/2016 | Vitaris et al. |
| 9,375,521 B2 | 6/2016 | Hudspeth et al. |
| 9,381,283 B2 | 7/2016 | Adams et al. |
| 9,414,968 B2 | 8/2016 | Heagle |
| 9,452,248 B2 | 9/2016 | Blott et al. |
| 9,844,475 B2 | 12/2017 | Hartwell |
| 9,925,313 B2 | 3/2018 | Weston |
| 10,123,909 B2 | 11/2018 | Hartwell |
| 10,207,035 B2 | 2/2019 | Weston |
| 11,045,598 B2 | 6/2021 | Greener |
| 11,701,266 B2 | 7/2023 | Greener |
| 2001/0029956 A1 | 10/2001 | Argenta et al. |
| 2001/0031911 A1 | 10/2001 | Khouri |
| 2001/0034499 A1 | 10/2001 | Sessions et al. |
| 2001/0038799 A1 | 11/2001 | Silver et al. |
| 2001/0043943 A1 | 11/2001 | Coffey |
| 2002/0002209 A1 | 1/2002 | Mork |
| 2002/0017304 A1 | 2/2002 | Heaton et al. |
| 2002/0026133 A1 | 2/2002 | Augustine et al. |
| 2002/0082567 A1 | 6/2002 | Lockwood et al. |
| 2002/0143286 A1 | 10/2002 | Tumey |
| 2002/0161317 A1 | 10/2002 | Risk et al. |
| 2002/0161346 A1 | 10/2002 | Lockwood et al. |
| 2002/0183702 A1 | 12/2002 | Henley et al. |
| 2002/0198504 A1 | 12/2002 | Risk, Jr. et al. |
| 2003/0021775 A1 | 1/2003 | Freeman |
| 2003/0023286 A1 | 1/2003 | Augustine et al. |
| 2003/0040687 A1 | 2/2003 | Boynton et al. |
| 2003/0045825 A1 | 3/2003 | Etheredge, III |
| 2003/0050594 A1 | 3/2003 | Zamierowski |
| 2003/0064190 A1 | 4/2003 | Carte et al. |
| 2003/0069529 A1 | 4/2003 | Augustine et al. |
| 2003/0069536 A1 | 4/2003 | Greter et al. |
| 2003/0069563 A1 | 4/2003 | Johnson |
| 2003/0125646 A1 | 7/2003 | Whitlock |
| 2003/0125649 A1 | 7/2003 | McIntosh et al. |
| 2003/0144619 A1 | 7/2003 | Augustine |
| 2003/0171675 A1 | 9/2003 | Rosenberg |
| 2003/0175798 A1 | 9/2003 | Raees et al. |
| 2003/0181824 A1 | 9/2003 | Odland |
| 2003/0188754 A1 | 10/2003 | Heaton et al. |
| 2003/0212357 A1 | 11/2003 | Pace |
| 2003/0212431 A1 | 11/2003 | Brady et al. |
| 2003/0219469 A1 | 11/2003 | Johnson et al. |
| 2003/0225347 A1 | 12/2003 | Argenta et al. |
| 2004/0006319 A1 | 1/2004 | Lina et al. |
| 2004/0019342 A1 | 1/2004 | Nagasuna et al. |
| 2004/0024351 A1 | 2/2004 | Greter et al. |
| 2004/0030304 A1 | 2/2004 | Hunt et al. |
| 2004/0039391 A1 | 2/2004 | Argenta et al. |
| 2004/0054338 A1 | 3/2004 | Bybordi et al. |
| 2004/0057855 A1 | 3/2004 | Gerlach et al. |
| 2004/0064111 A1 | 4/2004 | Lockwood et al. |
| 2004/0064132 A1 | 4/2004 | Boehringer et al. |
| 2004/0076662 A1 | 4/2004 | Riesinger |
| 2004/0087884 A1 | 5/2004 | Haddock et al. |
| 2004/0122434 A1 | 6/2004 | Argenta et al. |
| 2004/0126413 A1 | 7/2004 | Sigurjonsson et al. |
| 2004/0127862 A1 | 7/2004 | Bubb et al. |
| 2004/0127863 A1 | 7/2004 | Bubb et al. |
| 2004/0167482 A1 | 8/2004 | Watson |
| 2004/0171976 A1 | 9/2004 | Johnson |
| 2004/0241214 A1 | 12/2004 | Kirkwood et al. |
| 2004/0249353 A1 | 12/2004 | Risks, Jr. et al. |

(56) References Cited

U.S. PATENT DOCUMENTS

| | | |
|---|---|---|
| 2005/0012616 A1 | 1/2005 | Forster et al. |
| 2005/0013957 A1 | 1/2005 | Leschinsky |
| 2005/0016350 A1 | 1/2005 | Momose et al. |
| 2005/0020955 A1 | 1/2005 | Sanders et al. |
| 2005/0045461 A1 | 3/2005 | Sweetland et al. |
| 2005/0065471 A1 | 3/2005 | Kuntz |
| 2005/0085768 A1 | 4/2005 | Greter et al. |
| 2005/0090787 A1 | 4/2005 | Risk, Jr. et al. |
| 2005/0119737 A1 | 6/2005 | Bene et al. |
| 2005/0119739 A1 | 6/2005 | Glazier |
| 2005/0131327 A1 | 6/2005 | Lockwood et al. |
| 2005/0137539 A1 | 6/2005 | Biggie et al. |
| 2005/0165350 A1 | 7/2005 | Greter et al. |
| 2005/0177086 A1 | 8/2005 | Murata et al. |
| 2005/0228329 A1 | 10/2005 | Boehringer et al. |
| 2005/0245850 A1 | 11/2005 | Freyre et al. |
| 2005/0283105 A1 | 12/2005 | Heaton et al. |
| 2006/0009744 A1 | 1/2006 | Erdman et al. |
| 2006/0029650 A1 | 2/2006 | Coffey |
| 2006/0069365 A1 | 3/2006 | Sperl et al. |
| 2006/0070458 A1 | 4/2006 | Jones et al. |
| 2006/0079852 A1 | 4/2006 | Bubb et al. |
| 2006/0086598 A1 | 4/2006 | Sneek et al. |
| 2006/0107642 A1 | 5/2006 | Smith et al. |
| 2006/0149170 A1 | 7/2006 | Boynton et al. |
| 2006/0213527 A1 | 9/2006 | Argenta et al. |
| 2006/0259102 A1 | 11/2006 | Slatkine |
| 2006/0282028 A1 | 12/2006 | Howard et al. |
| 2007/0005028 A1 | 1/2007 | Risk, Jr. et al. |
| 2007/0021697 A1 | 1/2007 | Ginther et al. |
| 2007/0027414 A1 | 2/2007 | Hoffman et al. |
| 2007/0032762 A1 | 2/2007 | Vogel |
| 2007/0032778 A1 | 2/2007 | Heaton et al. |
| 2007/0038172 A1 | 2/2007 | Zamierowski |
| 2007/0040454 A1 | 2/2007 | Freudenberger et al. |
| 2007/0055209 A1 | 3/2007 | Patel et al. |
| 2007/0128055 A1 | 6/2007 | Lee |
| 2007/0167927 A1 | 7/2007 | Hunt et al. |
| 2007/0179460 A1 | 8/2007 | Adahan |
| 2007/0185463 A1 | 8/2007 | Mulligan |
| 2007/0219513 A1 | 9/2007 | Lina et al. |
| 2007/0225663 A1 | 9/2007 | Watt et al. |
| 2007/0255187 A1 | 11/2007 | Branch |
| 2007/0260207 A1 | 11/2007 | Ugander et al. |
| 2008/0009812 A1 | 1/2008 | Riesinger |
| 2008/0021356 A1 | 1/2008 | Castello Escude et al. |
| 2008/0031748 A1 | 2/2008 | Ihle et al. |
| 2008/0033352 A1 | 2/2008 | Annis et al. |
| 2008/0039761 A1 | 2/2008 | Heaton et al. |
| 2008/0045887 A1 | 2/2008 | Larsson et al. |
| 2008/0051716 A1 | 2/2008 | Stutz |
| 2008/0108977 A1 | 5/2008 | Heaton et al. |
| 2008/0132821 A1 | 6/2008 | Propp et al. |
| 2008/0167593 A1 | 7/2008 | Fleischmann |
| 2008/0200905 A1 | 8/2008 | Heaton et al. |
| 2008/0208147 A1 | 8/2008 | Argenta et al. |
| 2008/0223378 A1 | 9/2008 | Henderson et al. |
| 2008/0234641 A1 | 9/2008 | Locke et al. |
| 2008/0243044 A1 | 10/2008 | Hunt et al. |
| 2008/0294147 A1* | 11/2008 | Radl .............. A61M 1/913 604/543 |
| 2008/0306407 A1 | 12/2008 | Taylor |
| 2008/0306456 A1 | 12/2008 | Riesinger |
| 2008/0312572 A1 | 12/2008 | Riesinger |
| 2008/0312613 A1 | 12/2008 | Heaton et al. |
| 2009/0005746 A1 | 1/2009 | Nielsen et al. |
| 2009/0012441 A1 | 1/2009 | Mulligan |
| 2009/0012484 A1 | 1/2009 | Nielsen et al. |
| 2009/0036873 A1 | 2/2009 | Nielsen et al. |
| 2009/0048556 A1 | 2/2009 | Durand |
| 2009/0054855 A1 | 2/2009 | Blott et al. |
| 2009/0082740 A1 | 3/2009 | Lockwood et al. |
| 2009/0093779 A1 | 4/2009 | Riesinger |
| 2009/0124988 A1 | 5/2009 | Coulthard |
| 2009/0125004 A1 | 5/2009 | Shen et al. |
| 2009/0131892 A1 | 5/2009 | Karpowicz et al. |
| 2009/0137973 A1 | 5/2009 | Karpowicz et al. |
| 2009/0157024 A1 | 6/2009 | Song |
| 2009/0192467 A1 | 7/2009 | Hansen et al. |
| 2009/0198201 A1 | 8/2009 | Adahan |
| 2009/0204085 A1 | 8/2009 | Biggie et al. |
| 2009/0212723 A1 | 8/2009 | Toriyama et al. |
| 2009/0216170 A1 | 8/2009 | Robinson et al. |
| 2009/0216204 A1 | 8/2009 | Bhavaraju et al. |
| 2009/0221977 A1 | 9/2009 | Blott et al. |
| 2009/0227968 A1 | 9/2009 | Vess |
| 2009/0227969 A1* | 9/2009 | Jaeb .............. A61F 13/00063 604/313 |
| 2009/0234306 A1 | 9/2009 | Vitaris |
| 2009/0234309 A1 | 9/2009 | Vitaris et al. |
| 2009/0240185 A1 | 9/2009 | Jaeb et al. |
| 2009/0254053 A1 | 10/2009 | Svensby et al. |
| 2009/0254066 A1 | 10/2009 | Heaton et al. |
| 2009/0259203 A1 | 10/2009 | Hu et al. |
| 2009/0264807 A1* | 10/2009 | Haggstrom ....... A61F 13/00055 602/53 |
| 2009/0264837 A1 | 10/2009 | Adahan |
| 2009/0270820 A1 | 10/2009 | Johnson et al. |
| 2009/0287129 A1 | 11/2009 | Boehringer et al. |
| 2009/0293887 A1 | 12/2009 | Wilkes et al. |
| 2009/0299251 A1 | 12/2009 | Buan |
| 2009/0299255 A1 | 12/2009 | Kazala, Jr. et al. |
| 2009/0299306 A1 | 12/2009 | Buan |
| 2009/0306580 A1 | 12/2009 | Blott et al. |
| 2009/0312723 A1 | 12/2009 | Blott et al. |
| 2010/0004611 A1 | 1/2010 | Aali |
| 2010/0016767 A1 | 1/2010 | Jones et al. |
| 2010/0022972 A1 | 1/2010 | Lina et al. |
| 2010/0022990 A1 | 1/2010 | Karpowicz et al. |
| 2010/0030170 A1 | 2/2010 | Keller et al. |
| 2010/0030171 A1 | 2/2010 | Canada et al. |
| 2010/0030178 A1 | 2/2010 | MacMeccan et al. |
| 2010/0036334 A1 | 2/2010 | Heagle et al. |
| 2010/0063483 A1 | 3/2010 | Adahan |
| 2010/0069858 A1 | 3/2010 | Olson |
| 2010/0069863 A1 | 3/2010 | Olson |
| 2010/0087767 A1 | 4/2010 | McNeil |
| 2010/0100063 A1* | 4/2010 | Joshi .............. A61L 15/28 604/319 |
| 2010/0100160 A1 | 4/2010 | Edman et al. |
| 2010/0106112 A1 | 4/2010 | Vogel |
| 2010/0106117 A1 | 4/2010 | Lockwood et al. |
| 2010/0121286 A1 | 5/2010 | Locke et al. |
| 2010/0122417 A1 | 5/2010 | Vrzalik |
| 2010/0125258 A1 | 5/2010 | Coulthard et al. |
| 2010/0137775 A1 | 6/2010 | Hu et al. |
| 2010/0145289 A1 | 6/2010 | Lina et al. |
| 2010/0150991 A1 | 6/2010 | Bernstein |
| 2010/0159192 A1 | 6/2010 | Cotton |
| 2010/0160878 A1 | 6/2010 | Hunt et al. |
| 2010/0168633 A1 | 7/2010 | Bougherara et al. |
| 2010/0174251 A1 | 7/2010 | Weston |
| 2010/0191196 A1 | 7/2010 | Heagle |
| 2010/0191198 A1 | 7/2010 | Heagle |
| 2010/0207768 A1 | 8/2010 | Pidgeon et al. |
| 2010/0210986 A1 | 8/2010 | Sanders et al. |
| 2010/0228205 A1 | 9/2010 | Hu et al. |
| 2010/0249733 A9 | 9/2010 | Blott et al. |
| 2010/0262090 A1 | 10/2010 | Riesinger |
| 2010/0262091 A1 | 10/2010 | Larsson |
| 2010/0268198 A1 | 10/2010 | Buan et al. |
| 2010/0280468 A1 | 11/2010 | Haggstrom et al. |
| 2010/0280469 A1 | 11/2010 | Hall et al. |
| 2010/0286639 A1 | 11/2010 | Scholz et al. |
| 2010/0292632 A1 | 11/2010 | Mulvihill et al. |
| 2010/0305490 A1 | 12/2010 | Coulthard et al. |
| 2010/0305526 A1 | 12/2010 | Robinson et al. |
| 2010/0318043 A1 | 12/2010 | Malhi et al. |
| 2010/0318052 A1 | 12/2010 | Ha et al. |
| 2010/0324510 A1 | 12/2010 | Andresen et al. |
| 2011/0004172 A1 | 1/2011 | Eckstein et al. |
| 2011/0004173 A1 | 1/2011 | Hu et al. |
| 2011/0015593 A1 | 1/2011 | Svedman et al. |
| 2011/0022013 A1 | 1/2011 | Boynton et al. |

(56) References Cited

U.S. PATENT DOCUMENTS

| | | |
|---|---|---|
| 2011/0028918 A1 | 2/2011 | Hartwell |
| 2011/0028919 A1 | 2/2011 | Johnnison et al. |
| 2011/0028920 A1 | 2/2011 | Johannison |
| 2011/0028921 A1 | 2/2011 | Hartwell et al. |
| 2011/0034869 A1 | 2/2011 | Greter et al. |
| 2011/0034888 A1 | 2/2011 | Aali |
| 2011/0034892 A1 | 2/2011 | Buan |
| 2011/0034894 A1 | 2/2011 | Riesinger |
| 2011/0054422 A1 | 3/2011 | Locke et al. |
| 2011/0054423 A1 | 3/2011 | Blott et al. |
| 2011/0092927 A1 | 4/2011 | Wilkes et al. |
| 2011/0092958 A1 | 4/2011 | Jacobs |
| 2011/0105963 A1 | 5/2011 | Hu et al. |
| 2011/0106030 A1 | 5/2011 | Scholz |
| 2011/0112492 A1* | 5/2011 | Bharti .............. A61F 13/05 604/319 |
| 2011/0118683 A1 | 5/2011 | Weston |
| 2011/0125066 A1 | 5/2011 | Robinson et al. |
| 2011/0130712 A1 | 6/2011 | Topaz |
| 2011/0172617 A1 | 7/2011 | Riesinger |
| 2011/0224631 A1 | 9/2011 | Simmons et al. |
| 2011/0270201 A1 | 11/2011 | Bubb et al. |
| 2011/0270202 A1 | 11/2011 | Boehringer et al. |
| 2011/0282309 A1 | 11/2011 | Adie et al. |
| 2011/0313373 A1 | 12/2011 | Riesinger |
| 2011/0313374 A1 | 12/2011 | Lockwood et al. |
| 2012/0041399 A1 | 2/2012 | Blott et al. |
| 2012/0095380 A1 | 4/2012 | Gergely et al. |
| 2012/0109034 A1 | 5/2012 | Locke et al. |
| 2012/0109085 A1 | 5/2012 | McNeil |
| 2012/0130332 A1 | 5/2012 | Cotton et al. |
| 2013/0066285 A1 | 3/2013 | Locke et al. |
| 2013/0066289 A1 | 3/2013 | Song et al. |
| 2013/0090615 A1 | 4/2013 | Jaeb et al. |
| 2013/0090616 A1 | 4/2013 | Neubauer |
| 2013/0102979 A1 | 4/2013 | Coulthard et al. |
| 2013/0110058 A1 | 5/2013 | Adie et al. |
| 2013/0116635 A1 | 5/2013 | Fleischmann |
| 2013/0138054 A1 | 5/2013 | Fleischmann |
| 2013/0144230 A1 | 6/2013 | Wu et al. |
| 2013/0150814 A1 | 6/2013 | Buan |
| 2013/0165878 A1 | 6/2013 | Heagle |
| 2013/0274688 A1 | 10/2013 | Weston |
| 2013/0331822 A1 | 12/2013 | Patel et al. |
| 2014/0005618 A1 | 1/2014 | Locke et al. |
| 2014/0018753 A1 | 1/2014 | Joshi et al. |
| 2014/0114268 A1 | 4/2014 | Auguste et al. |
| 2014/0228791 A1 | 8/2014 | Hartwell |
| 2014/0236109 A1 | 8/2014 | Greener |
| 2014/0249493 A1 | 9/2014 | Hartwell |
| 2014/0316359 A1 | 10/2014 | Collinson et al. |
| 2014/0343519 A1 | 11/2014 | Weston |
| 2015/0032035 A1 | 1/2015 | Banwell et al. |
| 2015/0065965 A1 | 3/2015 | Haggstrom et al. |
| 2015/0073358 A1 | 3/2015 | Jaeb et al. |
| 2015/0174304 A1 | 6/2015 | Askem et al. |
| 2015/0202354 A1 | 7/2015 | Wall |
| 2015/0209492 A1 | 7/2015 | Blott et al. |
| 2015/0250931 A1 | 9/2015 | Bharti et al. |
| 2015/0258256 A1 | 9/2015 | Jaeb et al. |
| 2015/0308994 A1 | 10/2015 | Hammond et al. |
| 2016/0051737 A1 | 2/2016 | Joshi et al. |
| 2016/0081859 A1 | 3/2016 | Hartwell |
| 2016/0144084 A1 | 5/2016 | Collinson et al. |
| 2016/0166438 A1 | 6/2016 | Rovaniemi |
| 2016/0270967 A1 | 9/2016 | Hartwell |
| 2016/0298620 A1 | 10/2016 | Cordoba et al. |
| 2016/0317357 A1 | 11/2016 | Vitaris et al. |
| 2017/0095598 A1 | 4/2017 | Joshi et al. |
| 2017/0128642 A1 | 5/2017 | Buan |
| 2017/0181896 A1 | 6/2017 | Hartwell |
| 2017/0181897 A1 | 6/2017 | Hartwell |
| 2018/0311078 A1 | 11/2018 | Hartwell |

FOREIGN PATENT DOCUMENTS

| | | |
|---|---|---|
| DE | 3137839 A1 | 3/1983 |
| DE | 3032092 C2 | 10/1984 |
| DE | 3443101 A1 | 5/1986 |
| DE | 3935818 A1 | 5/1991 |
| DE | 4012232 A1 | 10/1991 |
| DE | 19844355 A1 | 4/2000 |
| DE | 202004017052 U1 | 6/2005 |
| EP | 0020662 B1 | 7/1984 |
| EP | 0257916 A1 | 3/1988 |
| EP | 0340018 A2 | 11/1989 |
| EP | 0355186 A1 | 2/1990 |
| EP | 0512543 A2 | 11/1992 |
| EP | 0619105 A1 | 10/1994 |
| EP | 0777504 B1 | 10/1998 |
| EP | 1013290 B1 | 6/2000 |
| EP | 1411874 A1 | 4/2004 |
| EP | 1455701 B1 | 3/2006 |
| EP | 1263366 B1 | 7/2006 |
| EP | 1726276 A2 | 11/2006 |
| EP | 1880840 A1 | 1/2008 |
| EP | 1476217 B1 | 3/2008 |
| EP | 1923077 A1 | 5/2008 |
| EP | 1955887 A2 | 8/2008 |
| EP | 1985270 A2 | 10/2008 |
| EP | 1121163 B1 | 11/2008 |
| EP | 1791579 B1 | 7/2009 |
| EP | 2098257 A1 | 9/2009 |
| EP | 1947987 B1 | 5/2010 |
| EP | 2185206 A2 | 5/2010 |
| EP | 1358456 B1 | 7/2010 |
| EP | 2214728 A2 | 8/2010 |
| EP | 2326295 A1 | 6/2011 |
| EP | 2335749 A1 | 6/2011 |
| EP | 2340064 A1 | 7/2011 |
| EP | 2346468 A2 | 7/2011 |
| EP | 2349155 A2 | 8/2011 |
| EP | 2205190 B1 | 9/2011 |
| EP | 2420214 A1 | 2/2012 |
| EP | 2021046 B1 | 3/2012 |
| EP | 2178573 B1 | 6/2012 |
| EP | 2462908 A1 | 6/2012 |
| EP | 2231088 B1 | 1/2013 |
| EP | 2015655 B1 | 3/2013 |
| EP | 2340066 B1 | 4/2013 |
| EP | 2340062 B1 | 6/2013 |
| EP | 1893145 B1 | 7/2013 |
| EP | 2263742 B1 | 9/2013 |
| EP | 1875081 B1 | 12/2013 |
| EP | 2271381 B1 | 12/2013 |
| EP | 2160166 B1 | 1/2014 |
| EP | 2305325 B1 | 4/2014 |
| EP | 2323712 B1 | 4/2014 |
| EP | 2345437 B1 | 4/2014 |
| EP | 2051675 B1 | 6/2014 |
| EP | 1485613 B1 | 7/2014 |
| EP | 2349154 B1 | 8/2014 |
| EP | 2146759 B1 | 9/2014 |
| EP | 2468323 B1 | 10/2014 |
| EP | 2544642 B1 | 1/2015 |
| EP | 2648668 A4 | 1/2015 |
| EP | 2249894 B1 | 8/2015 |
| EP | 2934402 A1 | 10/2015 |
| EP | 2293749 B1 | 8/2016 |
| EP | 2462956 B2 | 3/2017 |
| EP | 1587502 B1 | 5/2017 |
| EP | 1587554 B1 | 5/2017 |
| EP | 2227203 B1 | 9/2018 |
| EP | 3311856 B1 | 7/2019 |
| EP | 2355762 B1 | 9/2019 |
| EP | 2244756 B1 | 12/2019 |
| FR | 1163907 A | 10/1958 |
| FR | 2939320 A1 | 6/2010 |
| GB | 114754 A | 4/1918 |
| GB | 236350 A | 7/1925 |
| GB | 641061 A | 8/1950 |
| GB | 1224009 A | 3/1971 |
| GB | 1255395 A | 12/1971 |

(56) References Cited

FOREIGN PATENT DOCUMENTS

| | | |
|---|---|---|
| GB | 1400124 A | 7/1975 |
| GB | 1549756 A | 8/1979 |
| GB | 2061732 B | 6/1983 |
| GB | 2195255 A | 4/1988 |
| GB | 2307180 A | 5/1997 |
| GB | 2365350 A | 2/2002 |
| GB | 2378392 A | 2/2003 |
| GB | 2415908 A | 1/2006 |
| JP | S5986824 U | 6/1984 |
| JP | S5987824 U | 6/1984 |
| JP | S59165357 U | 11/1984 |
| JP | S6180018 A | 4/1986 |
| JP | S6180018 U | 5/1986 |
| JP | H04354722 A | 12/1992 |
| JP | 2003165843 A | 6/2003 |
| JP | 2005334188 A | 12/2005 |
| RU | 131622 U1 | 8/2013 |
| SU | 1251912 A1 | 8/1986 |
| WO | WO-8300742 A1 | 3/1983 |
| WO | WO-8401904 A1 | 5/1984 |
| WO | WO-9011795 A1 | 10/1990 |
| WO | WO-9100718 A1 | 1/1991 |
| WO | WO-9216245 A1 | 10/1992 |
| WO | WO-9220299 A2 | 11/1992 |
| WO | WO-9529959 A1 | 11/1995 |
| WO | WO-9605873 A1 | 2/1996 |
| WO | WO-9901173 A1 | 1/1999 |
| WO | WO-0007653 A1 | 2/2000 |
| WO | WO-0050143 A1 | 8/2000 |
| WO | WO-0059424 A1 | 10/2000 |
| WO | WO-0119430 A1 | 3/2001 |
| WO | WO-0134223 A1 | 5/2001 |
| WO | WO-0137922 A2 | 5/2001 |
| WO | WO-0185248 A1 | 11/2001 |
| WO | WO-0137922 A3 | 12/2001 |
| WO | WO-02083046 A1 | 10/2002 |
| WO | WO-02092783 A2 | 11/2002 |
| WO | WO-03092620 A2 | 11/2003 |
| WO | WO-2004024300 A1 | 3/2004 |
| WO | WO-2004037334 A1 | 5/2004 |
| WO | WO-2004077387 A1 | 9/2004 |
| WO | WO-2005009488 A2 | 2/2005 |
| WO | WO-2005016179 A2 | 2/2005 |
| WO | WO-2005025447 A2 | 3/2005 |
| WO | WO-2005025666 A2 | 3/2005 |
| WO | WO-2005046761 A1 | 5/2005 |
| WO | WO-2005051461 A1 | 6/2005 |
| WO | WO-2005070480 A1 | 8/2005 |
| WO | WO-2005079718 A1 | 9/2005 |
| WO | WO-2005082435 A1 | 9/2005 |
| WO | WO-2005105180 A1 | 11/2005 |
| WO | WO-2005123170 A1 | 12/2005 |
| WO | WO-2006048240 A1 | 5/2006 |
| WO | WO-2006048246 A1 | 5/2006 |
| WO | WO-2006052745 A2 | 5/2006 |
| WO | WO-2006052839 A2 | 5/2006 |
| WO | WO-2006056294 A1 | 6/2006 |
| WO | WO-2006081403 A1 | 8/2006 |
| WO | WO-2006116992 A1 | 11/2006 |
| WO | WO-2006133430 A2 | 12/2006 |
| WO | WO-2007002835 A2 | 1/2007 |
| WO | WO-2007013064 A1 | 2/2007 |
| WO | WO-2007019038 A2 | 2/2007 |
| WO | WO-2007024230 A1 | 3/2007 |
| WO | WO-2007030598 A2 | 3/2007 |
| WO | WO-2007030601 A2 | 3/2007 |
| WO | WO-2007084792 A2 | 7/2007 |
| WO | WO-2007085396 A1 | 8/2007 |
| WO | WO-2007092405 A2 | 8/2007 |
| WO | WO-2007106592 A2 | 9/2007 |
| WO | WO-2007133618 A2 | 11/2007 |
| WO | WO-2008013896 A2 | 1/2008 |
| WO | WO-2008027449 A2 | 3/2008 |
| WO | WO-2008039223 A1 | 4/2008 |
| WO | WO-2008040020 A2 | 4/2008 |
| WO | WO-2008041926 A1 | 4/2008 |
| WO | WO-2008100437 A1 | 8/2008 |
| WO | WO-2008100440 A1 | 8/2008 |
| WO | WO-2008112304 A1 | 9/2008 |
| WO | WO-2009019227 A2 | 2/2009 |
| WO | WO-2009019229 A2 | 2/2009 |
| WO | WO-2009047524 A2 | 4/2009 |
| WO | WO-2009062327 A1 | 5/2009 |
| WO | WO-2009066105 A1 | 5/2009 |
| WO | WO-2009066106 A1 | 5/2009 |
| WO | WO-2009089390 A2 | 7/2009 |
| WO | WO-2009098696 A2 | 8/2009 |
| WO | WO-2009103031 A1 | 8/2009 |
| WO | WO-2009111657 A2 | 9/2009 |
| WO | WO-2009117635 A1 | 9/2009 |
| WO | WO-2009120951 A2 | 10/2009 |
| WO | WO-2009122989 A1 | 10/2009 |
| WO | WO-2009124100 A1 | 10/2009 |
| WO | WO-2009126833 A2 | 10/2009 |
| WO | WO-2009146441 A1 | 12/2009 |
| WO | WO-2009147402 A2 | 12/2009 |
| WO | WO-2009151380 A1 | 12/2009 |
| WO | WO-2009156709 A1 | 12/2009 |
| WO | WO-2009158124 A1 | 12/2009 |
| WO | WO-2009158128 A1 | 12/2009 |
| WO | WO-2009158130 A1 | 12/2009 |
| WO | WO-2010026251 A1 | 3/2010 |
| WO | WO-2010051418 A2 | 5/2010 |
| WO | WO-2010072309 A1 | 7/2010 |
| WO | WO-2010072395 A1 | 7/2010 |
| WO | WO-2010120776 A1 | 10/2010 |
| WO | WO-2010141271 A1 | 12/2010 |
| WO | WO-2010142959 A2 | 12/2010 |
| WO | WO-2010147592 A1 | 12/2010 |
| WO | WO-2011019476 A1 | 2/2011 |
| WO | WO-2011023275 A1 | 3/2011 |
| WO | WO-2011130570 A1 | 10/2011 |
| WO | WO-2011135285 A1 | 11/2011 |
| WO | WO-2011135286 A1 | 11/2011 |
| WO | WO-2011135287 A1 | 11/2011 |
| WO | WO-2011144888 A1 | 11/2011 |
| WO | WO-2012022484 A1 | 2/2012 |
| WO | WO-2012041296 A2 | 4/2012 |
| WO | WO-2012131237 A1 | 10/2012 |
| WO | WO-2012140378 A1 | 10/2012 |
| WO | WO-2012143665 A1 | 10/2012 |
| WO | WO-2013010907 A1 | 1/2013 |
| WO | WO-2013083800 A1 | 6/2013 |
| WO | WO-2013090810 A1 | 6/2013 |
| WO | WO-2013136181 A2 | 9/2013 |
| WO | WO-2013149078 A1 | 10/2013 |
| WO | WO-2013175306 A2 | 11/2013 |
| WO | WO-2013175309 A1 | 11/2013 |
| WO | WO-2014008348 A2 | 1/2014 |
| WO | WO-2014016759 A1 | 1/2014 |
| WO | WO-2014020440 A1 | 2/2014 |
| WO | WO-2014020443 A2 | 2/2014 |
| WO | WO-2014099709 A1 | 6/2014 |
| WO | WO-2014108476 A1 | 7/2014 |
| WO | WO-2014113253 A1 | 7/2014 |
| WO | WO-2015022334 A1 | 2/2015 |
| WO | WO-2015022340 A1 | 2/2015 |
| WO | WO-2015031216 A1 | 3/2015 |
| WO | WO-2016107775 A2 | 7/2016 |
| WO | WO-2016182977 A1 | 11/2016 |

OTHER PUBLICATIONS

US 6,306,115 B1, 10/2001, Kelly et al. (withdrawn)
3M Tegaderm, "Transparent Film Dressings," Product Profile, filed in Opposition Proceedings for European Patent No. 2214610, mailed on Aug. 4, 2020, 8 pages.
Achterberg V., et al., "Hydroactive Dressings and Serum Proteins: An In Vitro Study," Journal of Wound Care, vol. 5 (2), Feb. 1996, pp. 79-82.
Advantec MFS, Inc., "Membrane Filters" (catalog), retrieved from http://www.advantecmfs.com/catalog/filt/membrane.pdf, on Jan. 29, 2016, Copyright 2001-2011, 17 pages.

(56) References Cited

OTHER PUBLICATIONS

Annex to the Communication, re the Opposition of European Patent No. EP2214610, dated Mar. 3, 2020, 17 pages.
Argenta L C., et al., "Vacuum-Assisted Closure: A New Method for Wound Control and Treatment: Clinical Experience," Annals of Plastic Surgery, vol. 38 (6), Jun. 1997, pp. 563-577.
Arnljots B., et al., "Irrigation Treatment in Split-Thickness Skin Grafting of Intractable Leg Ulcers," Scandinavian Journal of Plastic and Reconstructive Surgery, vol. 19, 1985, pp. 211-213.
Aubrey D.A., et al., "Treatment of the Perineal Wound after Proctectomy by Intermittent Irrigation," Arch. Surg, vol. 119, Oct. 1984, pp. 1141-1144.
Bagautdinov N.A., "Variant of External Vacuum Aspiration in the Treatment of Purulent Diseases of Soft Tissues," in Current Problems in Modern Clinical Surgery, Interdepartmental Collection, 1986, pp. 94-96.
BASF, Elastollan Physical Properties, 2020, 1 page.
Bragina, I.O., et al., "Radical Phenylation of Amides of Thiocinnamic Acid," Russian Chemical Bulletin, Dec. 31, 1983, 3 pages.
Brief Communication—Letter from the Opponent, re the Opposition of European Patent No. 3000448, dated Apr. 21, 2021, 3 pages.
Brief Communication—Letter from the Opponent, re the Opposition of European Patent No. EP2214611, dated Dec. 16, 2020, 5 pages.
Brief Communication—Letter from the Proprietor of the Patent, re the Opposition for Simmons & Simmons for European Patent No. 3000448, dated Apr. 23, 2021, 12 pages.
Brief Communication—Letter from the Proprietor of the Patent, re the Opposition for Simmons & Simmons for European Patent No. EP3254650, dated Mar. 5, 2021, 10 pages.
Brief Communication—Letter from the Proprietor of the Patent, re the Opposition of European Patent No. EP2214611, dated Dec. 17, 2020, 54 pages.
Brief Communication on Oral proceedings—Letter from the Opponent, re the Opposition of European Patent No. EP2214610, dated Feb. 26, 2021, 6 pages.
Chariker M.E., et al., "Effective Management of Incisional and Cutaneous Fistulae with Closed Suction Wound Drainage," Contemporary Surgery, vol. 34, Jun. 1989, pp. 59-63.
Chintamani et al., "Half Versus Full Vacuum Suction Drainage After Modified Radical Mastectomy for Breast Cancer—a Prospective Randomized Clinical Trial," BMC Cancer, Research Article, vol. 5(11), Jan. 27, 2005, 5 pages.
Communication of a Notice of Opposition and Opponent's Statement of Facts and Arguments for European Patent No. EP3254650, dated Sep. 30, 2020, 23 pages.
Davydov Y A., et al., "Concepts for Clinical Biological Management of the Wound Process in the Treatment of Purulent Wounds Using Vacuum Therapy," Vestnik Khirugii, Feb. 1991, pp. 15-17.
Davydov Y.A., et al., "Concepts of Clinico-Biological Management of Wound Process in Treatment of Purulent Wounds with the Help of Vacuum Therapy," Vestnik Chirurgia 1991, February Edition, pp. 132-135.
Davydov Y.A., et al., "The Bacteriological and Cytological Assessment of Vacuum Therapy of Purulent Wounds," Vestnik Khirurgii, Oct. 1988, pp. 11-14.
Davydov Y.A., et al., "Vacuum Therapy in the Treatment of Purulent Lactation Mastitis," The Kremlin Papers: Perspectives in Wound Care, Vestnik Khirurgii, BlueSky Publishing, 2004, pp. 5-7.
De Lange M.Y., et al., "Vacuum-Assisted Closure: Indications and Clinical Experience," Eur J Plast Surg (2000), vol. 23, Feb. 9, 2000, pp. 178-182.
Declaration of Chris Locke submitted in the Opposition against European Patent No. EP2563308, dated Sep. 7, 2016, 6 pages.
Dilmaghani A., et al., "A Method for Closed Irrigation and Suction Therapy in Deep Wound Infections," Journal of Bone and Joint Surgery, Mar. 1969, vol. 51-A(2), pp. 323-342.
Hartz R.S., et al., "Healing of the Perineal Wound," The Archives of Surgery, Apr. 1980, vol. 115, pp. 471-474.

Health Technology Literature Review, "Vacuum Assisted Closure Therapy for Wound Care," The Medical Advisory Secretariat, Dec. 2004, pp. 1-57.
Hersle K., et al., "Uses of Dextranomer Absorbent Pads After Cryosurgery of Cutaneous Malignancies," The Journal of Dermatologic Surgery and Oncology, vol. 8, Jan. 1982, pp. 35-37.
Interlocutory decision in Opposition proceedings (Art. 101(3)(a) and 106(2) EPC) for European patent No. 2214611, mailed on May 20, 2021, 87 pages.
International Preliminary Report on Patentability for Application No. PCT/GB2008/051089, mailed on May 25, 2010, 7 pages.
International Search Report for Application No. PCT/GB2008/051089, mailed on Mar. 4, 2009, 3 pages.
Invalidity Suit by *KCI Medizinprodukte GmbH* versus *Kalypto Medical, Inc.*, concerning declaration of invalidity of the German part of the European Patent No. 2021046 (German application No. 602007021330.4) dated Mar. 11, 2015 in 66 pages. EP2021046 is related to the present application by virtue of a common priority claim to U.S. Appl. No. 11/610,458, now U.S. Pat. No. 7,615,036, and U.S. Appl. No. 11/610,458, now U.S. Pat. No. 7,779,625.
Kalypto Medical, "NPD 1000 Negative Pressure Wound Care System," Clinician & Patient Instructions for Use, Feb. 2010, 36 pages.
Kalypto Medical, NPD 1000 Product Brochure (publication date unknown, believed to be Nov. 2010), 4 pages.
KCI Licensing Inc, "Prevena™ Incision Management System—Clinician Guide—Instructions for Use," 390061 Rev D, Jan. 2010, 10 pages.
KCI, "Prevena—Incision Management System Patient Guide," Jan. 2010, 2 pages.
KCI, "V.A.C. Freedom User's Guide," May 2002, 16 pages.
Kendall ULTEC Hydrocolloid Dressing (4×4), Product Ordering Page, web page downloaded on Jul. 13, 2014, 1 page.
Kennedy J.F., et al., "Advanced Textiles for Wound Care" (Second Edition), Chapter 10, 2019, 23 pages.
Khirugii V., "A Collection of Published Studies Complementing the Research and Innovation of Wound Care," The Kremlin Papers, Perspectives in Wound Care, Russian Medical Journal, Blue Sky Publishing, 2004, pp. 2-17.
Kostiuchenok B.M., et al., "The Vacuum Effect in the Surgical Treatment of Purulent Wounds," Russian Journal: Vestnik Khirurgii, Sep. 1986, pp. 18-21.
Minutes of the Oral Proceedings, Opposition Procedure and Summary of Facts and Submissions of European Patent No. 3000448, mailed on Jul. 22, 2021, 46 pages.
Morykwas M.J., et al., "Vacuum-Assisted Closure: A New Method for Wound Control and Treatment: Animal Studies and Basic Foundation," Annals Plastic Surgery, vol. 38 (6), Jun. 1997, pp. 553-562.
Notice of Opposition—Statement of Facts and Evidence of the European Patent No. 2214610, dated Jul. 8, 2019, 18 pages.
Notice of Response in Summons to Attend Oral Proceedings pursuant to rule 115(1) EPC for European Patent No. 2214611, mailed on Jun. 23, 2020, 19 pages.
Notice of Response in Summons to Attend Oral Proceedings pursuant to rule 115(1) EPC for European Patent No. 3000448, mailed on Jun. 23, 2020, 6 pages.
Nursing75., "Wound Suction: Better Drainage with Fewer Problems," Oct. 1975, pp. 52-53.
Nursing75., "Wound Suction: Better Drainage with Fewer Problems," vol. 5(10), Oct. 1975, pp. 52-55.
Opponent's Written Submission in Preparation for the Oral Proceedings, for the Opposition of European Patent No. 2214610, dated Sep. 25, 2020, 5 pages.
Proprietor's Written Submission in Preparation for the Oral Proceedings, for the Opposition of European Patent No. 2214610, dated Oct. 1, 2020, 20 pages.
Protz K., "Modern Wound Dressings Support the Healing Process," Wound care: Indications and Application, Geriatrie Journal, Apr. 2005, pp. 3333-3339 (17 pages with English translation).
Reply of the Patent Proprietor to the Notice of Opposition, re the Opposition of European Patent No. 2214610, dated Dec. 3, 2019, 25 pages.

(56) References Cited

OTHER PUBLICATIONS

Solovev V. A., et al., "The Method of Treatment of Immature External Fistulas in the Upper Gastrointestinal Tract—Guidelines," USSR Ministry of Health, S. M. Kirov Gorky State Medical Institute, 1987, 19 pages.
Solovev V.A., "Treatment and Prevention of Suture Failures after Gastric Resection," Dissertation Abstract, Gorky, 1988, 51 pages.
Stewart J., "World Wide Wounds—Next Generation of Products for Wound Management," Nov. 2002, http://www.worldwidewounds.com/2003/aprii/Stewart/Next-Generation-Products.html,13 pages.
Summons to Attend Oral Proceedings pursuant to rule 115(1) EPC and Preliminary Summary and Preliminary Opinion for Patent No. 3000448, mailed on Oct. 22, 2020, 9 pages.
Summons to Attend Oral Proceedings Pursuant to Rule 115(1) EPC for European Patent No. 3254650, dated Jul. 19, 2021, 13 pages.
Summons to attend oral proceedings pursuant to Rule 115(1) EPC for Patent No. EP2214610, mailed on Feb. 19, 2021, 17 pages.
Svedman P., "A Dressing Allowing Continuous Treatment of a Biosurface," IRCS Medical Science: Biomedical Technology; Clinical Medicine; Surgery and Transplantation, vol. 7, 1979, p. 221.
Svedman P., et al., "A Dressing System Providing Fluid Supply and Suction Drainage Used for Continuous or Intermittent Irrigation," Annals of Plastic Surgery, vol. 17 (2), Aug. 1986, 9 pages.
Svedman P., "Irrigation Treatment of Leg Ulcers," The Lancet, Sep. 3, 1983, pp. 532-534.
Swift S., et al., "Quorum Sensing in Aeromonas Hydrophila and Aeromonas Salmoncida: Identification of LuxRI Homologs AhyRI and AsaRI and Their Cognate N-Acylhomoserine Lactone Signal Molecules," Journal of Bacteriology, Sep. 1997, vol. 179, No. 17, pp. 5271-5281.
Technology Watch, May 1989, 1 page.
Teder H., et al., "Continuous Wound Irrigation in the Pig," Journal of Investigative Surgery, 1990, vol. 3, pp. 399-407.
Tribble D E., "An Improved Sump Drain-Irrigation Device of Simple Construction," Archives of Surgery, vol. 105, Sep. 1972, pp. 511-513.
Usupov Y. N., et al., "Active Wound Drainage," Russian Journal: Vestnik Khirurgii, Apr. 1987 (p. 42-45), Perspectives in Wound Care, BlueSky Publishing, pp. 8-10.
Venturi M L., et al., "Mechanisms and Clinical Applications of the Vacuum-Assisted Closure (VAC) Device," Am J Clin Dermatol, 2005, vol. 6, No. 3, pp. 185-194.
Viljanto J., et al., "Local Hyperalimentation of Open Wounds," Br. J. Surg., vol. 63, 1976, pp. 427-430.
Webb L X., "New Techniques in Wound Management: Vacuum-Assisted Wound Closure," Journal of the American Academy of Orthopaedic Surgeons, vol. 10, No. 5, Sep./Oct. 2002, pp. 303-311.
Westaby S., et al., "A Wound Irrigation Device," The Lancet, Sep. 2, 1978, pp. 503-504.
Wooding-Scott M., et al., "No Wound is Too Big for Resourceful Nurses," RN, Dec. 1988, pp. 22-25.
Written Submission by the Opponent re the Opposition Proceedings for European Patent No. 2214610, mailed on Aug. 4, 2021, 2 pages.
Written Submission by the Proprietor re the Opposition Proceedings for European Patent No. 2214610, mailed on Aug. 6, 2021, 23 pages.
Written Submissions in Preparation to Oral Proceedings, the Opposition of European Patent No. 3000448, dated Sep. 24, 2020, 10 pages.
Boards of Appeal—Letter of the opponent dated May 23, 2024 for European Patent No. 2214610, mailed on May 28, 2024, 4 pages.
Brief Communication—Letter from the Proprietor of the Patent, re the Opposition for Simmons & Simmons for European Patent No. 3360519, dated Jan. 3, 2022, 15 pages.
Brief Communication—Letter from the Opponent O1 of Jul. 14, 2023 for European Patent No. 3360519, mailed Jul. 19, 2023, 4 pages.
Brief Communication—Letter from the Opponent of the Patent, re the Opposition of European Patent No. EP3254650, dated Apr. 20, 2022, 5 pages.
Brief Communication—Letter from the Proprietor of the Patent for European Patent No. 3254650, mailed on Mar. 29, 2022, 2 pages.
Brief Communication—Letter from the Proprietor of the Patent of Jul. 14, 2023 for European Patent No. 3360519, mailed Jul. 19, 2023, 53 pages.
Brief Communication—Opposition proceedings filed in the Opposition against European Patent No. 2214610, mailed on Sep. 16, 2024, 7 pages.
Closure of the Appeal Proceedings withdrawal of the Appeal/Application/Opposition for European Patent No. 3254650, mailed on Jan. 11, 2024, 1 page.
Communication of the Board of Appeal pursuant to Article 15(1) for European Patent No. EP2214610, mailed Apr. 10, 2024, 12 pages.
Decision of the Board of Appeal of Jun. 14, 2024 filed in the opposition against European Patent No. 2214610, dated Jun. 17, 2024, 19 pages.
Decision revoking the European Patent (Art. 101 (3)(b) EPC) for European Patent No. 2214610, mailed on Nov. 15, 2021, 43 pages.
Decision to Maintain the Patent in Amended form for European Patent No. 3000448, dated Feb. 10, 2022, 1 page.
Forwarding of Submissions to Parties of a Letter of the Opponent for European Patent No. 2214610, dated Jul. 19, 2022, 12 pages.
Forwarding of Submissions to Parties of a Letter of the Opponent for European Patent No. 2214611, dated Feb. 7, 2022, 9 pages.
Forwarding of Submissions to parties of a letter of the Opponent for European Patent No. 3254650 dated Feb. 17, 2023 mailed on Feb. 23, 2023, 15 pages.
Information about the Result of Oral Proceedings for European Patent No. 3360519, mailed on Sep. 14, 2023, 2 pages.
Information about the Result of Oral Proceedings, the Opposition of European Patent No. 2214610, dated Oct. 8, 2021, 7 pages.
Letter Relating to the Appeal Procedure for European Patent No. 2214611, dated Mar. 30, 2022, 4 pages.
Letter relating to the Appeal Procedure for the Opposition of the European Patent No. 3254650, mailed on Apr. 17, 2023, 7 pages.
Notice of Opposition—Opponents' Statement of Facts and Arguments of the European Patent No. 3360519, dated Aug. 12, 2021, 12 pages.
Reply to Appeal—Letter of the patent proprietor for the European Patent No. 2214611, mailed on Jan. 24, 2022, 17 pages.
Reply to appeal by Simmons & Simmons filed in the opposition against European Patent No. 3360519, dated Jul. 18, 2024, 9 pages.
Reply to Opponent's Submission dated Jul. 13, 2022, for European Patent No. 2214610, mailed on Nov. 9, 2022, 6 pages.
Statement of Ground of Appeal filed by Opponent for European Patent No. 2214611 mailed on Sep. 20, 2021, 3 pages.
Statement of Grounds of Appeal filed by proprietor for European patent No. 2214611, mailed on Sep. 30, 2021, 46 pages.
Statement of Grounds of Appeal for the Opposition of European Patent No. 2214610, mailed on Mar. 8, 2022, 49 pages.
Summons to Attend Oral Proceedings pursuant to rule 115(1) EPC for the European Patent No. 3360519, mailed on Jul. 11, 2022, 18 pages.
Termination of Opposition Proceedings for European Patent No. 3000448, dated Feb. 4, 2022, 1 page.
Transmittal of Decision Summons for the Opposition of European Patent No. 3360519, mailed on Nov. 6, 2023, 55 pages.
Written Submission in Preparation to Oral Proceedings for European Patent No. 3360519, mailed on Aug. 2, 2023, 6 pages.
Letter dealing with Oral Proceedings during the Appeal Procedure for European Patent No. 2214610, mailed on Apr. 22, 2024, 2 pages.
Forwarding of Submissions to Parties of a Letter of the Patent Proprietor for European Patent No. 2214611, dated Dec. 14, 2023, mailed on Dec. 20, 2023, 7 pages.
Communication of the Board of Appeal pursuant to Article 15(1) for European Patent No. EP2214611, mailed Feb. 23, 2024, 7 pages.
Boards of Appeal—Letter of the opponent dated Mar. 25, 2024 for European Patent No. 2214611, mailed on Apr. 2, 2024, 4 pages.
Minutes of the Oral Proceedings of Apr. 16, 2024 for European Patent No. 2214611, mailed on Apr. 22, 2024, 5 pages.
Decision of Board of Appeal T 1165/21 Datasheet for the decision of Apr. 16, 2024 for European Patent No. 2214611, mailed on May 6, 2024, 05 pages.

(56) References Cited

OTHER PUBLICATIONS

Maintenance of the Patent with the Documents specified in the Final Decision, the Opposition of European Patent No. 3000448, mailed on Nov. 3, 2021, 1 page.
Information about the Result of Oral Proceedings for the Opposition of European Patent No. 3254650, mailed on Jun. 14, 2022, 4 pages.
Transmittal of Decision Summons for the Opposition of European Patent No. EP3254650, mailed on Jul. 13, 2022, 27 pages.
Statement of Grounds of Appeal for the European Patent No. 3254650, mailed on Nov. 7, 2022, 24 pages.
Statement of Grounds of Appeal for European Patent No. 3360519, mailed on Mar. 6, 2024, 66 pages.

* cited by examiner

WOUND DRESSING

CROSS-REFERENCE TO RELATED APPLICATIONS

This application is a continuation of U.S. application Ser. No. 16/186,393, filed Nov. 9, 2018, which is a continuation of U.S. application Ser. No. 14/692,622, filed Apr. 21, 2015, now U.S. Pat. No. 10,123,909, which is a continuation of U.S. application Ser. No. 14/276,983, filed May 13, 2014, now U.S. Pat. No. 9,220,822, which is a continuation of U.S. application Ser. No. 12/744,218, filed Sep. 20, 2010, now U.S. Pat. No. 8,808,274, which is the U.S. National Phase of PCT International Application No. PCT/GB2008/051089 filed on Nov. 20, 2008, designating the United States and published on May 28, 2009 as WO 2009/066105, which claims priority to Great Britain Patent Application No. 0722820.8, filed Nov. 21, 2007, and Great Britain Patent Application No. 0817040.9, filed Sep. 17, 2008. The disclosures of these prior applications are incorporated by reference in their entireties and should be considered a part of this specification.

BACKGROUND OF THE INVENTION

Field of the Invention

Any and all applications for which a foreign or domestic priority claim is identified in the Application Data Sheet as filed with the present application are hereby incorporated by reference under 37 CFR 1.57.

The present invention relates to a method and apparatus for dressing a wound and a method for manufacturing a wound dressing. In particular, but not exclusively, the present invention relates to a wound dressing useable during topical negative pressure (TNP) therapy in which the wound dressing itself acts as a waste canister to collect and store wound exudate removed from a wound site.

There is much prior art available relating to the provision of apparatus and methods of use thereof for the application of topical negative pressure (TNP) therapy to wounds together with other therapeutic processes intended to enhance the effects of the TNP therapy. Examples of such prior art include those listed and briefly described below.

TNP therapy assists in the closure and healing of wounds by reducing tissue oedema; encouraging blood flow and granulation of tissue; removing excess exudates and may reduce bacterial load and thus, infection to the wound. Furthermore, TNP therapy permits less outside disturbance of the wound and promotes more rapid healing.

In International patent application, WO 2004/037334, apparatus, a wound dressing and a method for aspirating, irrigating and cleansing wounds are described. In very general terms, the application describes the treatment of a wound by the application of TNP therapy for aspirating the wound together with the further provision of additional fluid for irrigating and/or cleansing the wound, which fluid, comprising both wound exudates and irrigation fluid, is then drawn off by the aspiration means and circulated through means for separating the beneficial materials therein from deleterious materials. The materials which are beneficial to wound healing are recirculated through the wound dressing and those materials deleterious to wound healing are discarded to a waste collection bag or vessel.

In International patent application, WO 2005/04670, apparatus, a wound dressing and a method for cleansing a wound using aspiration, irrigation and cleansing wounds are described. Again, in very general terms, the invention described in this document utilises similar apparatus to that in WO 2004/037334 with regard to the aspiration, irrigation and cleansing of the wound, however, it further includes the important additional step of providing heating means to control the temperature of that beneficial material being returned to the wound site/dressing so that it is at an optimum temperature, for example, to have the most efficacious therapeutic effect on the wound.

In International patent application, WO 2005/105180, apparatus and a method for the aspiration, irrigation and/or cleansing of wounds are described. Again, in very general terms, this document describes similar apparatus to the two previously mentioned documents hereinabove but with the additional step of providing means for the supply and application of physiologically active agents to the wound site/dressing to promote wound healing.

The content of the above-noted references is included herein by reference.

However, the above described apparatus and methods are generally only applicable to a patient when hospitalised as the apparatus used is complex, needing people having specialist knowledge in how to operate and maintain the apparatus, and also relatively heavy and bulky, not being adapted for easy mobility outside of a hospital environment by a patient, for example.

Some patients having relatively less severe wounds which do not require continuous hospitalisation, for example, but whom nevertheless would benefit from the prolonged application of TNP therapy, could be treated at home or at work subject to the availability of an easily portable and maintainable TNP therapy apparatus. To this end GB-A-2 307 180 describes a portable TNP therapy unit which may be carried by a patient and clipped to belt or harness. A negative pressure can thus be applied at a wound site.

During TNP therapy a portable or non-portable therapy unit generates a negative pressure at a wound site. As fluid, including air as well as wound exudate material is removed from the wound site this must be collected in some manner remote from the wound site. With prior known therapy units the collection and storage of wound exudate material is typically carried out by a waste canister connected to a pump unit of the therapy unit. The use of a canister, however, can result in the therapy unit apparatus itself being quite bulky and expensive to manufacture. Also replacing a canister or a bag in a canister in which wound exudate is collected can be a time consuming and relatively unhygienic process.

Prior known therapy units also tend to include a pump which is used to generate the negative pressure. Such pumps can be costly to manufacture and are relatively heavy.

WO 2007/030601, which is incorporated herein by reference discloses a self-contained wound dressing with a micro pump. The pump for drawing wound fluid into a vacuum zone is included in a wound dressing itself. Nevertheless wound exudate from the dressing can only be removed via a complex series of steps. The exudate removal process is also prone to contamination since once an absorbent layer is fully saturated with wound exudate an access door must be opened in the wound dressing so that the absorbent layer and micro pump can be removed. It will be appreciated that such exudate removal and pump removal can be time consuming and can lead to cross contamination between users. A further problem is that the wound dressing is prone to over expansion and rupture.

SUMMARY OF SOME EXEMPLIFYING EMBODIMENTS

It is an aim of the present invention to at least partly mitigate the above-mentioned problems.

It is an aim of certain embodiments of the present invention to provide a method for providing negative pressure at a wound site to aid in wound closure and healing in which wound exudate drawn from a wound site during the therapy is collected and stored in a wound dressing.

It is an aim of certain embodiments of the present invention to provide a wound dressing which is able to be placed over a wound site and which includes an integrated pump to generate negative pressure at that wound site. Also the wound dressing can collect any wound exudate.

According to a first aspect of the present invention there is provided apparatus for dressing a wound, comprising:
a sealing layer comprising at least one orifice;
an absorbent layer over the sealing layer for absorbing wound exudate; and
a liquid impermeable, gas permeable filter layer over the absorbent layer.

According to a second aspect of the present invention there is provided a method of applying topical negative pressure at a wound site, comprising the steps of:
via a pump element, pumping wound exudate and air from a wound site, a peripheral region around the wound site being sealed with a sealing layer of a wound dressing;
collecting wound exudate pumped from the wound site, through at least one orifice in the sealing layer, in an absorbent layer of the wound dressing; and
exhausting gas from the wound dressing through a filter layer between the absorbent layer and a cover layer extending over the wound dressing.

Certain embodiments of the present invention provide the advantage that a disposable wound dressing can be fixed over a wound site and can simultaneously be used to provide negative pressure at the wound site and collect and store wound exudate. A filter layer of the wound dressing permits air to be continually exhausted from the wound dressing as an integral pump or remote pump generates negative pressure at the wound site. This prevents a risk of over expansion.

Certain embodiments of the present invention provide the advantage that a separate therapy unit is not required to generate negative pressure at a wound site and collect and store any wound exudate. Rather a wound dressing can carry out both a pumping and wound exudate collecting process. The wound dressing may then be a one use item which can be disposed of subsequent to use. This reduces a risk of contamination.

Certain embodiments of the present invention provide the advantage that a wound dressing can be used to collect wound exudate generated during a negative pressure therapy process. A pump remote from the wound dressing can be connected to the wound dressing and reused whilst the wound dressing itself is used to collect wound exudate and may then be disposed of after use.

BRIEF DESCRIPTION OF THE DRAWINGS

Embodiments of the present invention will now be described hereinafter, by way of example only, with reference to the accompanying drawings in which.

DETAILED DESCRIPTION OF SOME EXEMPLIFYING EMBODIMENTS

Figure 1:
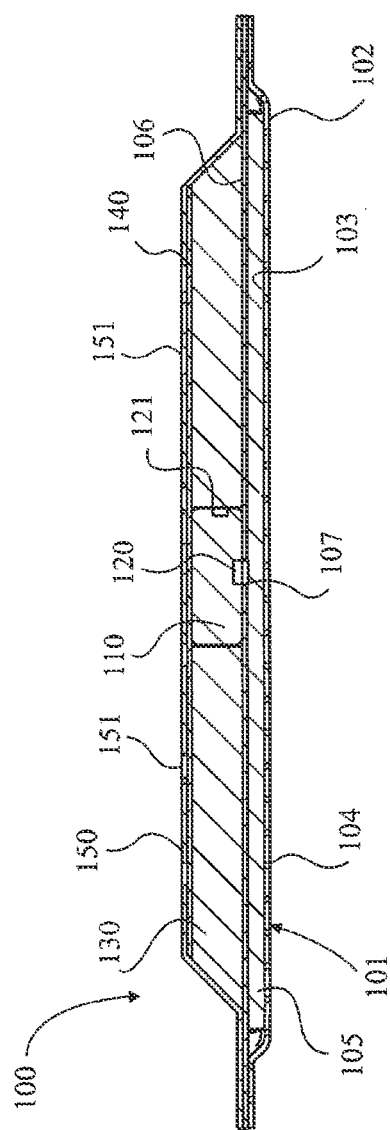
FIG. 1 illustrates a wound dressing.

In the drawings like reference numerals refer to like parts.

Figure 2:
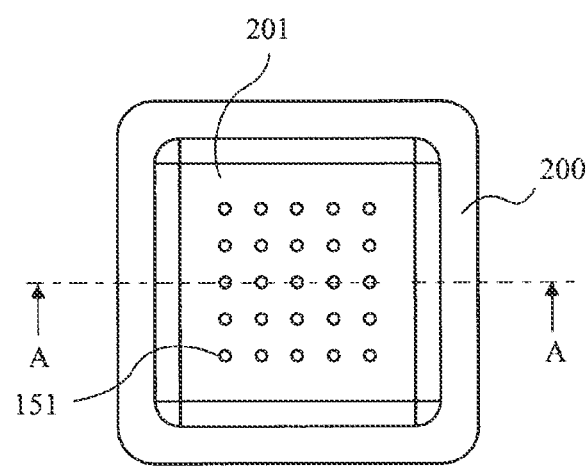
FIG. 2 illustrates a top view of a wound dressing.

FIG. 1 illustrates a cross section through a wound dressing 100 according to an embodiment of the present invention. A plan view from above of the wound dressing 100 is illustrated in FIG. 2 with the line A-A indicating the location of the cross section shown in FIG. 1. It will be understood that FIG. 1 illustrates a generalised schematic view of an apparatus 100. It will be understood that embodiments of the present invention are generally applicable to use in topical negative pressure (TNP) systems. Briefly, negative pressure wound therapy assists in the closure and healing of many forms of "hard to heal" wounds by reducing tissue oedema; encouraging blood flow and granular tissue formation; removing excess exudate and reducing bacterial load (and thus infection risk). In addition, the therapy allows for less disturbance of a wound leading to more rapid healing.

The wound dressing 100 can be located over a wound site to be treated. The dressing 100 forms a sealed cavity over the wound site. Optionally wound packer material can be used within a wound cavity below the dressing. Aptly the packer material can be a gauze or reticulated PU foam material.

It is envisaged that the negative pressure range for the apparatus embodying the present invention may be between about −50 mmHg and −200 mmHg (note that these pressures are relative to normal ambient atmospheric pressure thus, −200 mmHg would be about 560 mmHg in practical terms). Aptly the pressure range may be between about −75 mmHg and −150 mmHg. Alternatively a pressure range of up to −75 mmHg, up to −80 mmHg or over −80 mmHg can be used. Also aptly a pressure range of below −75 mmHg could be used. Alternatively a pressure range of over −100 mmHg could be used or over −150 mmHg.

As illustrated in FIG. 1 a lower surface 101 of the wound dressing 100 is provided by an optional wound contact layer 102. The wound contact layer 102 can be a polyurethane layer or polyethylene layer or other flexible layer which is perforated, for example via a hot pin process or in some other way, or otherwise made permeable to liquid and gas. The wound contact layer has a lower surface 101 and an upper surface 103. The perforations 104 are through holes in the wound contact layer which enables fluid to flow through the layer. The wound contact layer helps prevent tissue ingrowth into the other material of the wound dressing. The perforations are small enough to meet this requirement but still allow fluid through. The wound contact layer also helps hold the whole wound dressing together and acts as a carrier for an optional lower and upper adhesive layer (not shown). For example, a lower pressure sensitive adhesive may be provided on the underside surface 101 of the wound dressing whilst an upper pressure sensitive adhesive layer may be provided on the upper surface 103 of the wound contact layer. The pressure sensitive adhesive which may be a silicone or acrylic based adhesive or other such adhesives may be formed on both sides or optionally on a selected one or none of the sides of the wound contact layer. When a lower pressure sensitive adhesive layer is utilised this helps adhere the wound dressing to the skin around a wound site.

A layer 105 of porous material such as a foam layer or the like is located above the wound contact layer. This porous layer allows transmission of fluid including liquid and gas away from a wound site into upper layers of the wound dressing. The layer 105 also helps distribute pressure generated by a pump, mentioned in more detail below, so that a whole wound site sees an equalised negative pressure. Reticulated foam or a non-woven material which might be natural or synthetic can be used as the porous material of the porous layer 105.

A gas impermeable sealing layer 106 extends across the width of the wound dressing. The sealing layer which may, for example, be a polyurethane film having a pressure sensitive adhesive on both sides is impermeable to gas and this layer thus operates to seal a wound cavity over which the wound dressing is placed. In this way an effective chamber is made beneath the sealing layer and between the sealing layer and a wound site where a negative pressure can be established. Aptly whilst the sealing layer is gas impermeable the material of the sealing layer can have a high moisture vapour permeability. For example Elastollan (Trade name) SP9109 manufactured by BASF. A dotted pattern spread acrylic adhesive can optionally be used to help improve moisture vapour permeability. An advantage of using a high moisture vapour permeability material as the sealing layer 160 is that the fluid handling capacity of the dressing may be increased significantly by the action of moisture transpiring through the film and dispersing into the atmosphere. Advantageously, transpiration rates can be easily achieved of the order of 3000 grams/centimetre square/ 24 hours as a result of the high humidity achieved in the dressing and intimate contact of material achieved during use of the apparatus at a negative pressure of up to 250 mmHg below atmospheric pressure.

As illustrated in FIG. 1 a single central orifice is provided in the sealing layer. It will be appreciated that as an alternative the single orifice 107 may be provided as a plurality of through holes. The orifice 107 enables a micro pump 1 10 with associated valves not shown, which is integral to the wound dressing, to suck fluid from a region beneath the sealing layer 106 into a region above the sealing layer 106. A pump inlet is located in a facing relationship to the orifice 107 whilst an outlet 121 of the pump 1 10 is arranged to exhaust fluid pumped through the pump into a layer 130 of absorbent material. The absorbent material which may be a foam or non-woven natural or synthetic material and which may optionally include or be superabsorbent material forms a reservoir for fluid, particularly liquid, removed from the wound site. The material of the absorbent layer also prevents liquid collected in the wound dressing from flowing in a sloshing manner. The absorbent layer 130 also helps distribute fluid throughout the layer via a wicking action so that fluid is drawn from a region proximate to the exhaust outlet 121 of the pump into more remote regions so that agglomeration near the pump exit is avoided.

A filter layer 140 is provided over the absorbent layer 130. A suitable material for the filter material of the filter layer 140 is 0.2 micron Gore™ expanded PTFE from the MMT range. Larger pore sizes can also be used but these may require a secondary filter layer to ensure full bioburden containment. As wound fluid contains lipids it is preferable, though not essential, to use an oleophobic filter membrane for example 1.0 micron MMT-332 prior to 0.2 micron MMT-323. This prevents the lipids from blocking the hydrophobic filter.

It will be understood that other types of material could be used for the filter layer. More generally a microporous membrane can be used which is a thin, flat sheet of polymeric material, this contains billions of microscopic pores. Depending upon the membrane chosen these pores can range in size from 0.01 to more than 10 micrometers. Microporous membranes are available in both hydrophilic (water filtering) and hydrophobic (water repellent) forms. Aptly the wound dressing 100 according to certain embodiments of the present invention uses microporous hydrophobic membranes (MHMs). Numerous polymers may be employed to form MHMs. For example, PTFE, polypropylene, PVDF and acrylic copolymer. All of these optional polymers can be treated in order to obtain specific surface characteristics that can be both hydrophobic and oleophobic. As such these will repel liquids with low surface tensions such as multi-vitamin infusions, lipids, surfactants, oils and organic solvents.

MHMs block liquids whilst allowing air to flow through the membranes. They are also highly efficient air filters eliminating potentially infectious aerosols and particles. A single piece of MHM is well known as an option to replace mechanical valves or vents. Incorporation of MHMs can thus reduce product assembly costs improving profits and costs/benefit ratio to a patient.

The filter layer 140 thus enables gas to be exhausted upwards through the wound dressing. Liquid, particulates and pathogens, however, are contained in the dressing.

A cover layer 150 covers the absorbent layer of the wound dressing 100. The cover layer which, for example, may be a polyurethane film acts as a bacterial barrier and helps hold in liquid to stop fouling. The cover layer is sealed to the filter layer. For example via adhesive or welding techniques. Gas leaving the dressing thus passes through the filter layer and then the holes 151 in the cover layer. The cover layer also provides integrity for the dressing and is permeable to moisture vapour and gas by virtue of through holes 151 provided in the cover layer, for example by way of an array of perforations. These help improve the permeability to moisture vapour and gas through the wound dressing. In an alternative embodiment the filter layer 140 may instead cover the whole dressing sealing with the sealing layer 106. A protector layer or reinforcing layer may be included (this may be a non-woven or perforated film). Aptly the cover layer 150 is made from a material having a high moisture vapour permeability. For example Elastollan (Trade name) SP9109 manufactured by BASF. A dotted pattern spread acrylic adhesive can optionally be used to help improve moisture vapour permeability. An advantage of using a high moisture vapour permeability material as the cover layer 160 is that the fluid handling capacity of the dressing may be increased significantly by the action of moisture transpiring through the film and dispersing into the atmosphere. Advantageously, transpiration rates can be easily achieved of the order of 3000 grams/centimetre square/24 hours as a result of the high humidity achieved in the dressing and intimate contact of material achieved during use of the apparatus at a negative pressure of up to 250 mmHg below atmospheric pressure.

Turning to FIG. 2 which illustrates a wound dressing 100 in accordance with an embodiment of the present invention one can see an upper surface of the cover layer 150 which extends radially outwardly away from a centre of the dressing into a border region 200 surrounding a central raised region 201 overlying the absorbent layer 130. FIG. 2 also helps illustrate the array of perforations 151 formed in the cover layer.

Figure 3:
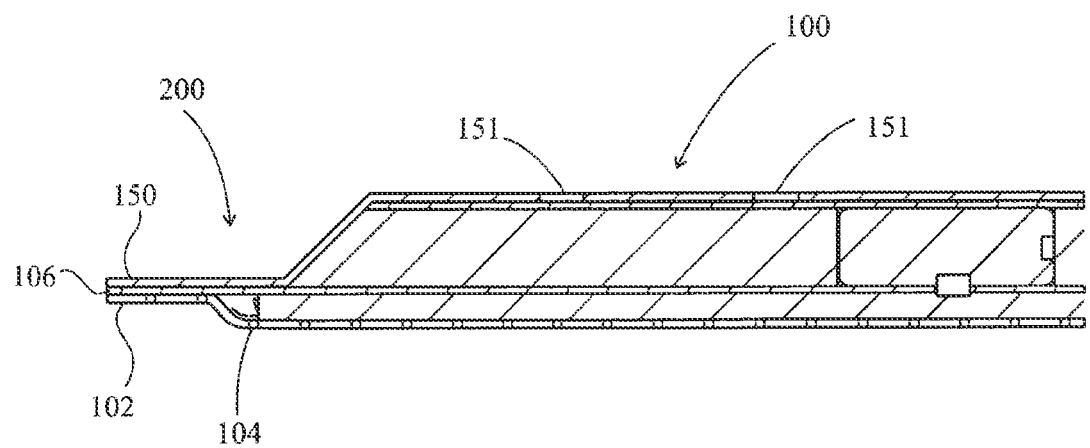
FIG. 3 illustrates a portion of the wound dressing.

FIG. 3 illustrates an expanded view of the border region 200 of the wound dressing 100 illustrated in FIGS. 1 and 2. As seen, the cover layer 150 extends over the absorbent layer 130 into an edge region. Here the cover layer is secured to the sealing layer 106 and the wound contact layer 102. FIG. 3 also helps illustrate how the perforations 104 in the wound contact layer 102 extend around the foam layer 105.

It will be understood that according to embodiments of the present invention the wound contact layer is optional. This layer is, if used, porous to water and faces an underlying wound site. A lower porous layer 105 such as a reticulated PU foam layer is used to distribute gas and fluid removal such that all areas of a wound are subjected to equal pressure. The sealing layer forms a substantially airtight seal over the wound. Thus as the pump 1 10 pumps a negative pressure is generated below the sealing layer. This negative pressure is thus experienced at the target wound site. Fluid including air and wound exudate is drawn through the wound contact layer and reticulated foam layer through the orifice 107 and into a fluid inlet 120 at the pump 1 10. The pump exhausts the fluid through a fluid exit 121 where the liquid component is wicked away so as to be collected and stored throughout the absorbent layer 130. The gaseous components of the exhausted fluid, together with some moisture vapour, are exhausted through the filter layer and through the perforations of the cover layer. The filter layer ensures that pathogens and unpleasant odours do not leave the reservoir region formed by the absorbent layer.

It will be appreciated by those skilled in the art that rather than have a cover layer overlying the filter layer the cover layer may itself be overlain by a filter layer. The cover layer may thus be the outermost layer of the wound dressing or the filter layer may be the outermost layer of the wound dressing. Further outer layers (not shown) may optionally be used so long as they are gas and water vapour permeable.

As still further options the dressing can contain antimicrobial e.g. nanocrystalline silver agents on the wound contact layer and/or silver sulphur diazine in the absorbent layer. These may be used separately or together. These respectively kill micro-organisms in the wound and micro-organisms in the absorption matrix. As a still further option other active components, for example, pain suppressants, such as ibuprofen, may be included. Also agents which enhance cell activity, such as growth factors or that inhibit enzymes, such as matrix metalloproteinase inhibitors, such as tissue inhibitors of metalloproteinase (TIMPS) or zinc chelators could be utilised. As a still further option odour trapping elements such as activated carbon, cyclodextrine, zealite or the like may be included in the absorbent layer or as a still further layer above the filter layer.

Figure 4:
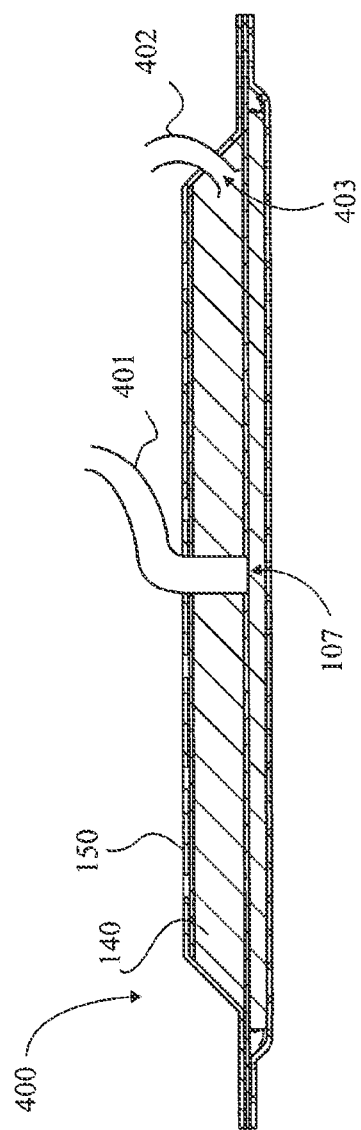
FIG. 4 illustrates a wound dressing with an external pump.

FIG. 4 illustrates an alternative embodiment of the present invention in which a pump is not provided integral within a wound dressing 400. Rather a connecting tube 401 is connected to an orifice 107 in the sealing layer. The outlet tube 401 is sealed around its outer circumference to the cover layer 150 and filter layer 140. The outlet conduit 401 is connected to a remote pump which may be some distance from the wound dressing 400 or may be mounted to a border of the wound dressing. An outlet of the remote pump is secured to an inlet tube 402 which is sealed about its circumference to a cover layer 150 leading to an opening 403. In this way as a pump is operated to apply a negative pressure to a zone below the sealing layer 106 exudate is drawn through the wound contact layer 102 and lower fluid distribution layer 105 through the orifice 107 and along the exit tube 401. Fluid, including air and wound exudate, passes through the pump and is exhausted in a region proximate to the opening 403 in outlet tube 402. The liquid part of the fluid is wicked away to be collected in the body of the absorbent layer 130. Air and moisture vapour passes through the filter layer and through the apertures in the cover layer into the ambient atmosphere.

It will be understood that according to embodiments of the present invention as fluid is drawn from a wound site the absorbent layer may expand. This may result in a slight bulge appearing in the upper surface of the filter and cover layer. In many respects the bulge can be used as a visible cue to indicate when a wound dressing should be replaced.

As mentioned above with respect to the embodiment shown in FIG. 4 a remote pump may be mounted to a border of the wound dressing in which case the tubes 401, 402 may be connected directly to the pump. Subsequent to a single use the wound dressing and pump may thus be discarded. As an option the tubes may be provided with a click fit connector or other easy fit connector which can be connected to corresponding mating connectors joined via corresponding tubes to a remote pump. In this way a remote pump may be reused whilst the wound dressing itself including connecting tubes and connectors is disposable after a single use.

It will be understood that for embodiments of the present invention which include a pump mounted on the cover layer or on a peripheral border area of the dressing an integral power source and control circuitry can be included. Alternatively the power source can be external to the pump and remotely mounted. A remote power source and/or control circuitry improves the disposability of the dressing and permits battery recharge if spare batteries are used.

It will also be appreciated that in use the dressing may be used "up-side down", at an angle or vertical. References to upper and lower are thus used for explanation purposes only.

It will be appreciated that alternatively the tubes 401, 402 could be a single dual lumen tube. As a still further alternative the tubes 401, 402 could alternatively be a single continuous looped tube, the tube then passing through pinch rollers for a peristaltic pump.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

What is claimed is:

1. An apparatus for the treatment of a wound by applying negative pressure to the wound, the apparatus comprising:
    a first porous layer for disposing on the wound, wherein the first porous layer comprises a first side and a second, patient-facing side;
    a sealing layer disposed over the first side of the porous layer to form a sealed space over the wound containing the first porous layer, wherein the sealing layer comprises a high-moisture vapor permeable material;
    a second porous layer having a first side and a second, patient-facing side;
    a cover layer disposed over the first side of the second porous layer forming an enclosure;
    at least one port formed on the cover layer; and
    a negative pressure source configured to be fluidly coupled to the sealed space and to the enclosure.

2. The apparatus of claim 1, wherein the at least one port is configured to allowing air to exit the enclosure.

3. The apparatus of claim 1, wherein the negative pressure source comprises a pump configured to be fluidly coupled to the sealed space and to the enclosure.

4. The apparatus of claim 1, further comprising a filter coupled to the at least one port.

5. The apparatus of claim 1, further comprising a pump for producing a reduced pressure and an exhaust, and wherein the pump is fluidly coupled to the sealed space for delivering the reduced pressure thereto and fluidly coupled to the enclosure for delivering the exhaust thereto.

6. The apparatus of claim 1, further comprising:
a first opening fluidly coupled to the sealed space;
a second opening fluidly coupled to the channel space;
a first reduced-pressure conduit fluidly coupled to the first interface; and
a second conduit fluidly coupled to the second interface; and
a pump for producing a reduced pressure, the negative pressure source comprising the pump, wherein the pump is fluidly coupled to the first reduced-pressure conduit and to the second conduit to deliver the reduced pressure to the first reduced-pressure conduit.

7. An apparatus for the treatment of a wound by applying negative pressure to the wound, the apparatus comprising:
a housing comprising a sealing layer and a cover layer,
a sealed space formed by the housing, wherein the sealed space comprises a first chamber and a second chamber; and
a vacuum pump disposed within the sealed space, the vacuum pump comprises a reduced-pressure outlet fluidly coupled to the second chamber and an exhaust outlet fluidly coupled to the first chamber;
wherein the cover layer comprises at least in part a filter layer, wherein the filter layer comprises a polymeric, porous, hydrophobic material for allowing the exhaust gas to exit the positive-pressure chamber through the filter layer.

8. The apparatus of claim 7, wherein the filter layer comprises an odor trapping material.

9. The apparatus of claim 7, wherein the second chamber comprises a reduced pressure chamber.

\* \* \* \* \*